US010828455B2

(12) United States Patent
Graham et al.

(10) Patent No.: US 10,828,455 B2
(45) Date of Patent: Nov. 10, 2020

(54) MEDICAL TUBES AND METHODS OF MANUFACTURE

(71) Applicant: Fisher & Paykel Healthcare Limited, Auckland (NZ)

(72) Inventors: Peter Kenneth Graham, Auckland (NZ); Enrico Alvarez Garcia, Auckland (NZ); David John Sims, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 390 days.

(21) Appl. No.: 14/351,344

(22) PCT Filed: Oct. 12, 2012

(86) PCT No.: PCT/NZ2012/000184
§ 371 (c)(1),
(2) Date: Apr. 11, 2014

(87) PCT Pub. No.: WO2013/055235
PCT Pub. Date: Apr. 18, 2013

(65) Prior Publication Data
US 2014/0373840 A1 Dec. 25, 2014

Related U.S. Application Data

(60) Provisional application No. 61/547,482, filed on Oct. 14, 2011.

(51) Int. Cl.
*A61M 16/08* (2006.01)
*A61M 16/10* (2006.01)
(Continued)

(52) U.S. Cl.
CPC .... *A61M 16/0875* (2013.01); *A61M 16/0003* (2014.02); *A61M 16/021* (2017.08);
(Continued)

(58) Field of Classification Search
CPC ......... A61M 16/00–0096; A61M 16/08–0891; A61M 16/16–168; A61M 16/20;
(Continued)

(56) References Cited

U.S. PATENT DOCUMENTS 3,871,373 A * 3/1975 Jackson ................ A61M 15/08
128/203.27
4,000,341 A * 12/1976 Matson ................. A61M 16/08
128/200.24
(Continued)

FOREIGN PATENT DOCUMENTS

CN 101438088 5/2009
CN 101541367 9/2009
(Continued)

OTHER PUBLICATIONS

International Search Report; PCT/NZ2012/000184; dated Jan. 23, 2013; 3 pages.
(Continued)

*Primary Examiner* — Samchuan C Yao
*Assistant Examiner* — Ned T Heffner
(74) *Attorney, Agent, or Firm* — Knobbe, Martens, Olson & Bear, LLP

(57) ABSTRACT

This invention relates to a medical tube comprises an elongate conduit having a first opening, a second opening, a longitudinal axis, a lumen extending between the first opening and the second opening along the longitudinal axis, and a corrugated wall, formed from an extruded material, extending between the first opening and the second opening and surrounding the lumen. The wall is stiffer in a first length of the conduit adjacent the first opening than in a second length of the conduit adjacent the second opening. The variable stiffness of the tube wall can improve the thermal profile of the tube as well as improve drain-back of con-
(Continued)

densation into a humidifier providing humidified gas to the tube.

24 Claims, 15 Drawing Sheets

(51) Int. Cl.
| | |
|---|---|
| *A61M 16/16* | (2006.01) |
| *A61M 39/08* | (2006.01) |
| *A61M 16/00* | (2006.01) |
| *A61M 16/06* | (2006.01) |
| A61M 13/00 | (2006.01) |
| B29L 23/00 | (2006.01) |
| B29L 31/00 | (2006.01) |
| B29C 48/30 | (2019.01) |
| B29C 48/151 | (2019.01) |
| B29C 48/09 | (2019.01) |
| B29C 48/00 | (2019.01) |

(52) U.S. Cl.
CPC .......... *A61M 16/06* (2013.01); *A61M 16/109* (2014.02); *A61M 16/1095* (2014.02); *A61M 16/16* (2013.01); *A61M 39/08* (2013.01); A61M 13/003 (2013.01); A61M 16/0841 (2014.02); A61M 16/1075 (2013.01); A61M 2205/0238 (2013.01); A61M 2205/3368 (2013.01); A61M 2205/3633 (2013.01); A61M 2205/75 (2013.01); A61M 2207/00 (2013.01); A61M 2207/10 (2013.01); A61M 2209/02 (2013.01); B29C 48/0016 (2019.02); B29C 48/09 (2019.02); B29C 48/151 (2019.02); B29C 48/30 (2019.02); B29C 48/303 (2019.02); B29L 2023/007 (2013.01); B29L 2031/7542 (2013.01)

(58) Field of Classification Search
CPC ........ A61M 16/04; A61M 16/041–048; A61M 39/00; A61M 39/10; A61M 16/208; A61M 11/00; A61M 11/001; A61M 11/02; A61M 11/04; A61M 11/041–048; F24F 6/00; F16L 11/00–26
See application file for complete search history.

(56) References Cited

U.S. PATENT DOCUMENTS

| | | | | |
|---|---|---|---|---|
| 5,143,409 | A * | 9/1992 | Lalikos | F16L 35/00 285/114 |
| 5,623,922 | A | 4/1997 | Smith | |
| 5,640,951 | A | 6/1997 | Huddart et al. | |
| 5,848,223 | A * | 12/1998 | Carlson | A61M 16/1095 219/528 |
| 6,026,811 | A * | 2/2000 | Settle | A61M 16/0666 128/207.17 |
| 6,427,694 | B1 * | 8/2002 | Hecker | A61M 16/06 128/201.22 |
| 2002/0010277 | A1 * | 1/2002 | Kaulbach | C08L 27/18 525/200 |
| 2004/0102731 | A1 | 5/2004 | Blackhurst et al. | |
| 2005/0011524 | A1 * | 1/2005 | Thomlinson | A61M 16/0666 128/207.18 |
| 2005/0165366 | A1 | 7/2005 | Brustad et al. | |
| 2006/0254662 | A1 | 11/2006 | Rivest et al. | |
| 2008/0028850 | A1 * | 2/2008 | Payton | A61M 16/1075 73/204.19 |
| 2008/0032119 | A1 * | 2/2008 | Feldhahn | A61M 16/06 428/332 |
| 2008/0060649 | A1 * | 3/2008 | Veliss | A61M 16/06 128/205.25 |
| 2008/0105257 | A1 * | 5/2008 | Klasek | A61M 16/0633 128/203.27 |
| 2011/0247619 | A1 | 10/2011 | Formica et al. | |

FOREIGN PATENT DOCUMENTS

| | | |
|---|---|---|
| EP | 1075848 A2 | 2/2001 |
| EP | 2039386 A1 | 3/2009 |
| EP | 2215962 A1 | 8/2010 |
| EP | 2283889 A2 | 2/2011 |
| JP | 2007-524480 | 8/2007 |
| JP | 8-109984 | 5/2008 |
| WO | WO 1991-011381 A1 | 8/1991 |
| WO | WO 2003-022342 A1 | 3/2003 |
| WO | WO 2008/055308 A1 | 5/2008 |
| WO | WO 2008/060587 A2 | 5/2008 |
| WO | WO 2009-098244 A2 | 8/2009 |
| WO | WO 2011/149362 A1 | 12/2011 |
| WO | WO 2011/162622 A1 | 12/2011 |
| WO | WO 2012/033421 A1 | 3/2012 |

OTHER PUBLICATIONS

China First Office Action; 201280058622.9; dated Sep. 2, 2015; 44 pages.
Supplemental European Search Report; PCT/NZ2012/000184; dated Apr. 17, 2015; 7 pages.
Chinese Second Office Action; dated Jun. 29, 2016; 5 pages.
EPO Examination Report; dates May 25, 2016; 5 pages.
Australian Examination Report; dated Sep. 15, 2016; 3 pages.
Office Action dated Jun. 14, 2017 in European Patent Application No. 12840138.7 in 4 pages.
Examination Report No. 1 for Standard Patent Application for Australian Application 2017272155 dated Mar. 25, 2019 in 6 pages.

* cited by examiner

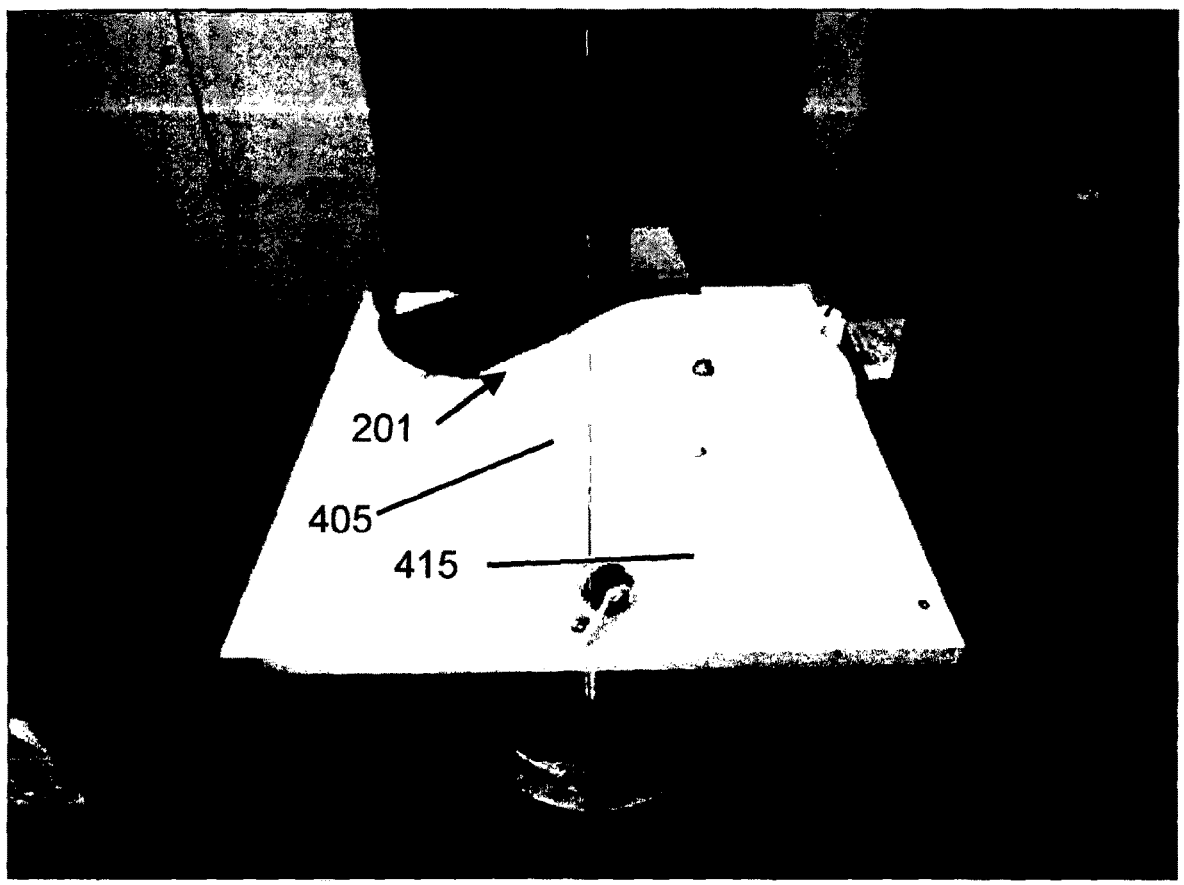
FIG. 4C
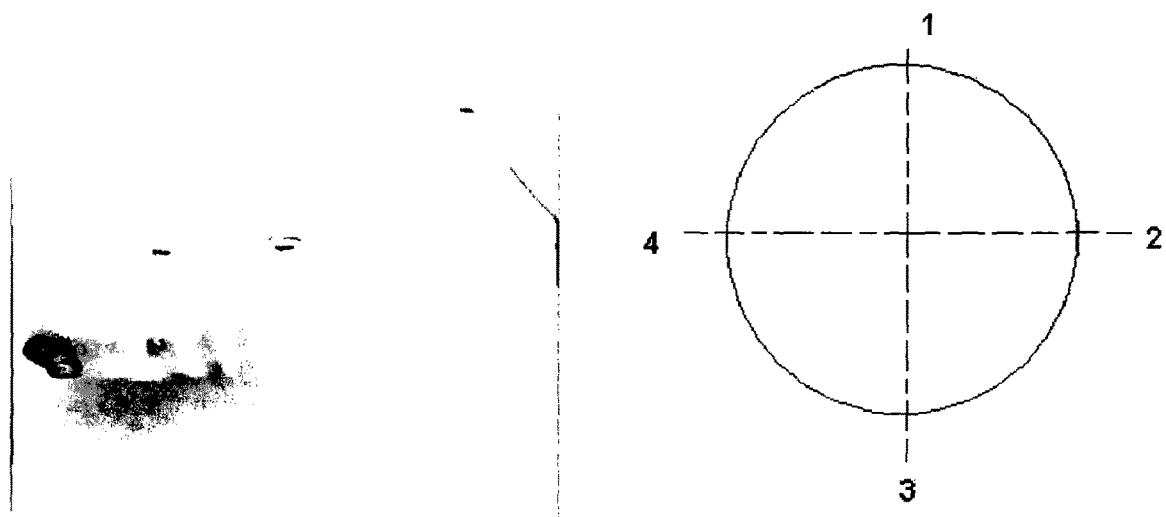
FIG. 4D  FIG. 4E

MEDICAL TUBES AND METHODS OF MANUFACTURE

FIELD OF INVENTION

This disclosure relates generally to tubes suitable for medical use, and in particular to tubes for use in medical circuits suitable for providing gases to and/or removing gases from a patient, such as in positive airway pressure (PAP), respirator, anesthesia, ventilator, and insufflation systems.

BACKGROUND TO THE INVENTION

In medical circuits, various components transport warm, humidified gases to patients. For example, in some breathing circuits such as PAP or assisted breathing circuits, gases inhaled by a patient are delivered from a heater-humidifier through an inspiratory tube. As another example, tubes can deliver humidified gas (commonly $CO_2$) into the abdominal cavity in insufflation circuits. This can help prevent "drying out" of the patient's internal organs, and can decrease the amount of time needed for recovery from surgery.

In these medical applications, the gases are preferably delivered in a condition having humidity near saturation level and at close to body temperature (usually at a temperature between 33° C. and 37° C.). Condensation or "rain-out" can form on the inside surfaces of the breathing tubes as the high humidity breathing gases cool and/or come into contact with the relatively cooler breathing tube surface. A need remains for tubing that insulates against heat loss and, for example, allows for improved temperature and/or humidity control in medical circuits.

It is therefore an object of the present invention to provide a medical tube and/or method of manufacturing a medical tube which will go at least some way towards addressing the foregoing problems or which will at least provide the industry or public or both with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description which is given by way of example only.

SUMMARY OF THE INVENTION

Medical tubes and breathing tubes and methods of manufacturing such tubes are disclosed herein in various embodiments.

In least one embodiment, a medical tube for providing humidified gas to a patient can comprise an elongate conduit having a first opening configured in size and shape to connect to a source of humidified gas, a second opening configured in size and shape to connect to a patient interface, a longitudinal axis, a lumen extending between the first opening and the second opening along the longitudinal axis, and a wall, formed from an extruded material, extending between the first opening and the second opening and surrounding the lumen. The wall is stiffer in a first region of the conduit adjacent the first opening than in a second region of the conduit adjacent the second opening.

In at least one embodiment, a heated breathing tube can comprise a single, corrugated extruded conduit comprising a proximal, patient end and a distal, chamber end; and one or more heating elements on or in the conduit, wherein the conduit has a first region at the chamber end with a first stiffness and a second region at the patient end with a second stiffness and the first stiffness is greater than the second stiffness.

In various embodiments, in the foregoing medical tube and/or heated breathing tube, the first region is configured to extend vertically from a source of humidified gas. The vertical extension can define a drain-back length. The drain-back length can be between about 350 mm and about 400 mm, for instance.

In various embodiments, the foregoing medical tube and/or heated breathing tube have one, some, or all of the following properties, as well as properties described elsewhere in this disclosure. The medical or breathing tube can further comprise one or more conductive filaments in or on the conduit. At least one of the one or more conductive filaments can be a heating wire. At least one of the one or more conductive filaments can be a sensing wire. The conduit can be generally cylindrical. The wall can be corrugated. The extruded material can be foam. The foam can be polymer foam. The foam can be closed-cell foam. The extruded material can comprise one or more surface modification agents. The wall can have an average contact angle less than 50 degrees (or about 50 degrees). The thickness of the wall in the first region can be between 0.5 mm and 2.0 mm (or about 0.5 mm and about 2.0 mm). The thickness of the wall in the second region can be between 0.1 mm and 1.0 mm (or about 0.1 mm and about 1.0 mm). The mass of the wall in the first region can be between 50 g/m and 110 g/m (or about 50 g/m and about 110 g/m). The weight of the wall in the second region can be between 20 g/m and 50 g/m (or about 20 g/m and about 50 g/m). The volume of the wall in the first region can be between 1.0 cm3/m and 2.0 cm3/m (or about 1.0 cm3/m and about 2.0 cm3/m). The volume of the wall in the second region is between about 0.2 cm3/m and about 1.0 cm3/m. The ratio of flex modulus of the wall in the first region to flex modulus of the wall in the second region can be between 10:1 and 250:1 (or about 10:1 and about 250:1). Stiffness of the wall in a third region of the conduit between the first region and the second region can be intermediate the stiffness of the wall in the first region and the second region. The average wall thickness can be about 100 microns.

In various embodiments, the foregoing medical tube or heated breathing tube (including any or all of the above properties) have one, some, or all of the following properties, as well as properties described elsewhere in this disclosure. The medical or breathing tube can further comprise a sheath surrounding at least a portion of an outer surface the elongate conduit. The sheath can comprise an extruded material extruded around at least a portion of the outer surface of the elongate conduit. The sheath can comprise a material generally spirally wrapped around at least a portion of the outer surface of the elongate conduit. The sheath can comprise a sleeve material sleeved around at least a portion of the outer surface of the elongate conduit. The sheath can comprise a sheath wall. The sheath wall can have a generally constant stiffness. The sheath wall can be stiffer in a first region of the sheath than in a second region of the sheath. The sheath wall can be stiffer proximate the first opening of the conduit than the second opening of the conduit. The sheath wall can be stiffer proximate the second opening of the conduit than the first opening of the conduit. The sheath wall can be stiffer proximate the first opening and second opening of the conduit than in an intermediate region of the conduit.

The foregoing medical tube according to an or all of the preceding embodiments can be incorporated into a breathing circuit or an insufflation system, among other applications. The breathing tube can be incorporated into a breathing circuit, among other applications.

In at least one embodiment, a method of delivering humidified gas to a patient can comprise providing a single, corrugated extruded conduit comprising a proximal, patient end, a distal, chamber end, heating elements on or in the conduit wall, a first region adjacent the chamber end with a first stiffness, and a second region adjacent the patient end with a second stiffness, the first stiffness being greater than the second stiffness; connecting the chamber end of the conduit to a chamber, wherein the conduit in the first region extends vertically from the chamber; connecting the patient end of the conduit to a patient interface; and delivering humidified air through the conduit. In various embodiments, the conduit can have one, some, or all of the properties described above with respect to the medical and breathing tubes, as well as properties described elsewhere in this disclosure.

In at least one embodiment, a method of manufacturing a tube or conduit according to one, some, or all of the above embodiments comprises extruding a tape, wherein a first length of the tape is thicker, heavier, or stiffer than a second length of the tape; spirally winding the extruded tape around a mandrel such that adjacent turns of the extruded tape touch or overlap, thereby forming an elongate conduit having a longitudinal axis and a lumen extending along the longitudinal axis; corrugating and cooling the elongate conduit to form the medical tube, the tube having a wall surrounding the lumen, wherein the wall is stiffer in a first region of the conduit adjacent a first end than in a second region of the conduit adjacent the second end. As explained above, the wall can have a thickness between 0.5 mm and 2.0 mm (or about 0.5 mm and about 2.0 mm in the first region). The wall can have a thickness between 0.1 mm and 1.0 mm (or about 0.1 mm and about 1.0 mm) in the second region. The ratio of flex modulus of the wall in the first region to flex modulus of the wall in the second region can be between about 10:1 and about 250:1.

In various embodiments, the foregoing method can have one, some, or all of the above tube or conduit properties, following properties, as well as properties described elsewhere in this disclosure. The extruded tape can comprise foam. The foam can be polymer foam. The polymer foam can be closed cell. The extruded tape can comprise one or more surface modification agents. A surface of the wall facing the lumen can have a surface contact angle less than 50 degrees (or about 50 degrees). The method can further comprise spirally winding a reinforcement bead between adjacent turns of the extruded tape. The reinforcement bead can comprise one or more conductive filaments. The method can further comprises spirally winding one or more conductive filaments around the elongate conduit.

In at least one embodiment, a method of manufacturing a tube or conduit according to one, some, or all of the foregoing embodiments comprises extruding an elongate conduit having a longitudinal axis and a lumen extending along the longitudinal axis; and corrugating and cooling the elongate conduit to form the medical tube, the tube having a wall surrounding the lumen, wherein the wall is stiffer in a first region of the conduit adjacent a first end than in a second region of the conduit adjacent the second end. In various embodiments, the foregoing method can have one, some, or all of the above tube or conduit properties, the following properties, as well as properties described elsewhere in this disclosure. As explained above, the first region can be configured to extend vertically from a source of humidified gas. The vertical extension can define a drain-back length. The drain-back length can be between 350 mm and 400 mm (or about 350 mm to about 400 mm). In certain embodiments, the method can further comprise co-extruding one or more conductive filaments, such that the one or more conductive filaments are disposed on or in the conduit.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIGS. 4A-4E illustrates test equipment for measuring the flex modulus of tubes.

Throughout the drawings, reference numbers are re-used to indicate correspondence between referenced (or similar)

elements. In addition, the first digit of each reference number indicates the figure in which the element first appears.

DETAILED DESCRIPTION

Details regarding several illustrative embodiments for implementing the apparatuses and methods described herein are described below with reference to the figures. The invention is not limited to these described embodiments.

Breathing Circuit Comprising One or More Medical Tubes

Figure 1:
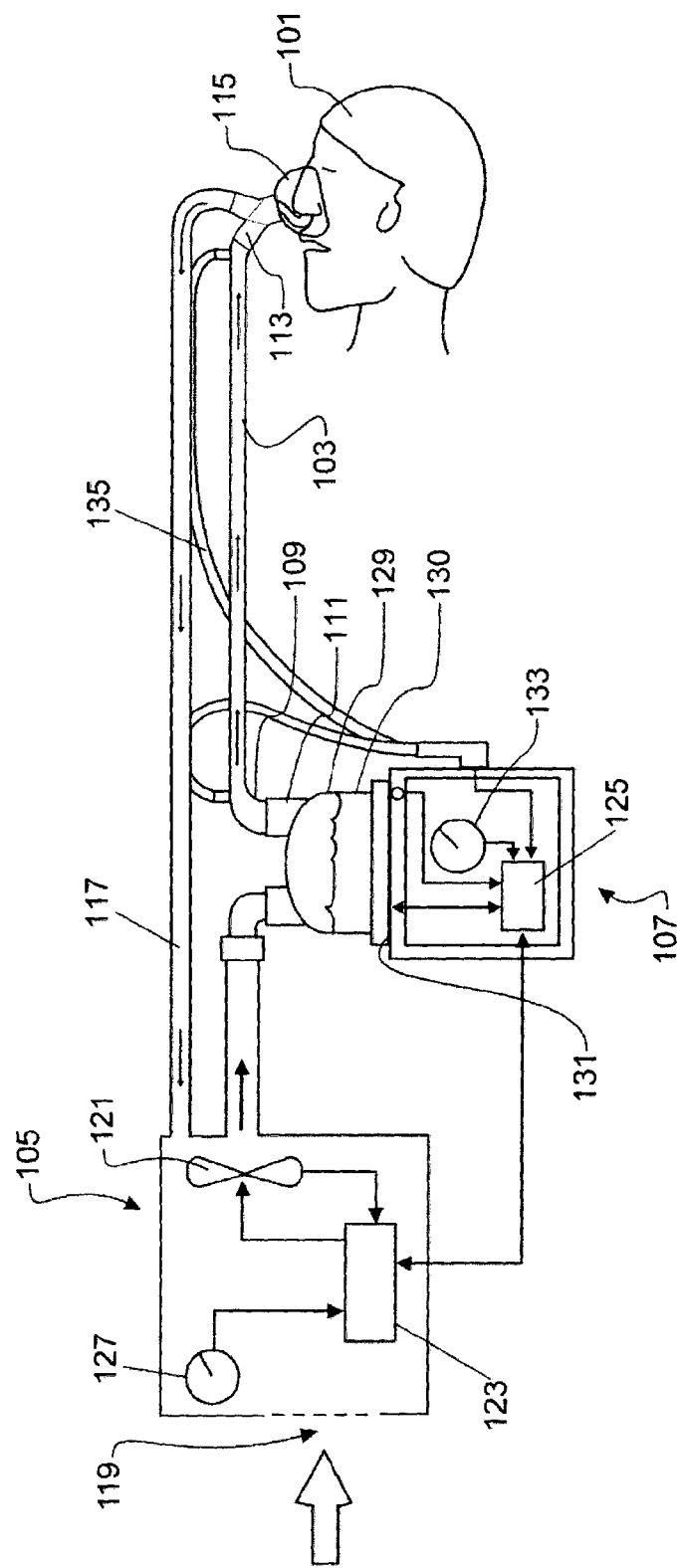
FIG. 1 shows a schematic illustration of a medical circuit incorporating one or more medical tubes.

For a more detailed understanding of the disclosure, reference is first made to FIG. 1, which shows a breathing circuit according to at least one embodiment, which includes one or more medical tubes. Tube is a broad term and is to be given its ordinary and customary meaning to a person of ordinary skill in the art (that is, it is not to be limited to a special or customized meaning) and includes, without limitation, non-cylindrical passageways. The breathing circuit incorporates one or more variable-stiffness tubes, which may generally be defined as a tube having distinct stiffness at each end of the tube. Such a breathing circuit can be a continuous, variable, or bi-level positive airway pressure (PAP) system or other form of respiratory therapy.

Gases can be transported in the circuit of FIG. 1 as follows. Dry gases pass from a ventilator/blower 105 to a humidifier 107, which humidifies the dry gases. The humidifier 107 connects to the inlet 109 (the end for receiving humidified gases) of the inspiratory tube 103 via a port 111, thereby supplying humidified gases to the inspiratory tube 103. An inspiratory tube is a tube that is configured to deliver breathing gases to a patient, and may be made from a variable-stiffness tube as described in further detail below. The gases flow through the inspiratory tube 103 to the outlet 113 (the end for expelling humidified gases), and then to the patient 101 through a patient interface 115 connected to the outlet 113.

An expiratory tube 117 also connects to the patient interface 115. An expiratory tube is a tube that is configured to move exhaled humidified gases away from a patient. Here, the expiratory tube 117 returns exhaled humidified gases from the patient interface 115 to the ventilator/blower 105.

In this example, dry gases enter the ventilator/blower 105 through a vent 119. A fan 121 can improve gas flow into the ventilator/blower by drawing air or other gases through vent 119. The fan 121 can be, for instance, a variable speed fan, where an electronic controller 123 controls the fan speed. In particular, the function of the electronic controller 123 can be controlled by an electronic master controller 125 in response to inputs from the master controller 125 and a user-set predetermined required value (preset value) of pressure or fan speed via a dial 127.

The humidifier 107 comprises a humidification chamber 129 containing a volume of water 130 or other suitable humidifying liquid. Preferably, the humidification chamber 129 is removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. But the humidification chamber 129 can also include conductive components. For instance, the humidification chamber 129 can include a highly heat-conductive base (for example, an aluminum base) contacting or associated with a heater plate 131 on the humidifier 107. By way of example, the humidifier 107 may be a standalone humidifier, such as any of the humidifiers in the respiratory humidification range of Fisher & Paykel Healthcare Limited of Auckland, New Zealand.

The humidifier 107 can also include electronic controls. In this example, the humidifier 107 includes an electronic, analog or digital master controller 125. Preferably, the master controller 125 is a microprocessor-based controller executing computer software commands stored in associated memory. In response to the user-set humidity or temperature value input via a user interface 133, for example, and other inputs, the master controller 125 determines when (or to what level) to energize heater plate 131 to heat the water 130 within humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows. A temperature probe 135 can connect to the inspiratory tube 103 near the patient interface 115, or to the patient interface 115. The temperature probe 135 monitors the temperature near or at the patient interface 115. A heating filament (not shown) associated with the temperature probe can be used to adjust the temperature of the patient interface 115 and/or inspiratory tube 103 to raise the temperature of the inspiratory tube 103 and/or patient interface 115 above the saturation temperature, thereby reducing the opportunity for unwanted condensation.

In FIG. 1, exhaled humidified gases are returned from the patient interface 115 to the ventilator/blower 105 via the expiratory tube 117. The expiratory tube 117 can also be a variable-stiffness tube, as described in greater detail below. However, the expiratory tube 117 can also be a medical tube as previously known in the art. In either case, the expiratory tube 117 can have a temperature probe and/or heating filament, as described above with respect to the inspiratory tube 103, integrated with it to reduce the opportunity for condensation. Furthermore, the expiratory tube 117 need not return exhaled gases to the ventilator/blower 105. Alternatively, exhaled humidified gases can be passed directly to ambient surroundings or to other ancillary equipment, such as an air scrubber/filter (not shown). In certain embodiments, the expiratory tube is omitted altogether.

Variable-Stiffness Tubes

Figure 2A:
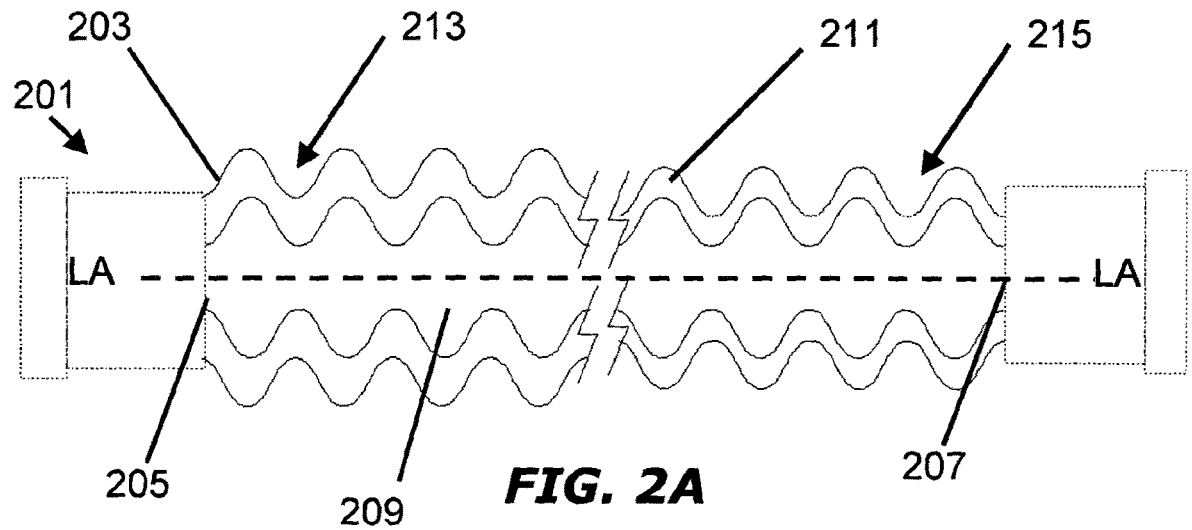
FIGS. 2A-2C show longitudinal cross sections of example composite tubes.

FIG. 2A shows a longitudinal cross section of example variable-thickness tube 201. In general, the medical tube 201 comprises an elongate conduit 203 having a first opening 205, a second opening 207, and a longitudinal axis LA-LA. In this example, the elongate conduit 203 has a generally cylindrical shape. Nevertheless, "conduit" is a broad term and is to be given its ordinary and customary meaning to a person of ordinary skill in the art (that is, it is not to be limited to a special or customized meaning) and includes, without limitation, non-cylindrical passageways. A lumen 209 extends between the first opening 205 and the second opening 207 along the longitudinal axis LA-LA. The conduit 203 is stiffer adjacent the first opening 205 than it is adjacent the second opening 207.

The conduit 203 comprises a wall 211, extending between the first opening 205 and the second opening 207, and surrounding the lumen 209. In this example, the wall 211 is stiffer in a first region 213 of the conduit 203 adjacent the first opening 205 than in a second region 215 of the conduit 203 adjacent the second opening 207. The wall 211 can be optionally corrugated, or of a corrugate profile. As shown in this example, the corrugation profile can comprise of alternating outer crests (or annular protrusions) and inner troughs (or annular recesses). The outer crests can correspond to a location of maximum inner radius and maximum outer radius of the elongate conduit, and the inner troughs can correspond to a location of minimum inner radius and minimum outer radius of the elongate conduit. Such corrugations may be of an annular corrugation or spiral corrugation form. Alternatively, the wall 211 can be of a smooth or non-corrugated profile. Optionally, the first opening 205 is configured in size and shape to connect to a source of humidified gas, such as a humidifier described above, and the second opening 207 is configured in size and shape to connect to a patient interface. For instance, one or more ends can be configured to connect to a connection port which facilitates connection to the patient interface and/or humidifier. Other configurations can also be desirable. For example, in other embodiments, the first opening 205 can be configured to connect to a patient interface, while the second opening 207 can be configured to connect to a ventilator/blower, as described above.

As described in greater detail below, the tube 201 can optionally include one or more conductive (heating or sensing) filaments. Optional positions for the filaments are: placed within the lumen, typically in a loose, spiral fashion; placed in close external contact to the tube wall, typically in conjunction with an external sheath to secure the conductive filaments) in place and prevent heat loss; or embedded in the tube wall.

The increased stiffness of the tube at one end can lead to better management of condensate by improving "drain back." Furthermore, the increased stiffness is linked to properties that improve the insulating profile of the wall, such as increased thickness, mass, and/or volume. Thus, for unheated tubes or tubes with heating filaments placed within the lumen, the first end is preferably the humidifier end to better insulate the tube against heat loss where most of the condensation occurs. This configuration also adds stiffness to the tube where it exits the humidifier, so it can maintain a more vertical position for a greater distance, before bending toward the horizontal. In this way, more condensation drains back to the humidifier, rather than entering the breathing tube. A thinner tube at the patient end improves flexibility, reduces weight, and improves the comfort of the patient.

For heating filaments placed externally (e.g., on the tube wall radially opposite the lumen) or embedded in the wall, the second end is preferably the humidifier end to allow heat from the elements to more easily penetrate the tube and heat the gas stream. An insulating external sheath (described below) will typically be fitted to this type of tube to prevent heat loss. A stiffer tube at the patient end is offset by a thinner sheath to increase flexibility and reduce weight to improve the user's comfort.

Thus, in use, the tubes according to the various embodiments lead to less condensate and also a greater range of ambient conditions where they can be used before condensation build up becomes a substantial issue.

In general, the total length of the tube can be between 1.0 m and 3.0 m (or about 1.0 m and 3.0 m) or between 1.0 and 2.0 m (or about 1.0 and 2.0 m). Preferably, the length of the tube is 1.5 m (or about 1.5 m) or 1.8 m (or about 1.8 m). Preferably, the average diameter of the lumen (accounting for the variability in diameter created by the crests and troughs in optional corrugation) is between 10 mm and 30 mm (or about 10 mm and 30 mm). Preferably, the lumen diameter is 20 mm (or about 20 mm) or 22 mm (or about 22 mm). In fact, it is contemplated that the variable-stiffness tubes described herein can be used as a replacement for tubes previously used in the art, which typically have an average lumen diameter between 10 mm and 30 mm and length ranging between about 1 m and 2.5 m.

It is also preferable that the tube be resistant to crushing, resistant to restrictions in flow when bent, resistant to kinking, resistant to changes in length and/or volume under internal pressure, resistant to leaking (<25 mL/min at 6 kPa), have low flow resistance (the increase in pressure at maximum rated flow is less than 0.2 kPa), and be electrically safe. Preferably, the tube can be bent around a 25 mm diameter metal cylinder without kinking, occluding, or collapsing, as defined in the test for increase in flow resistance with bending according to ISO 5367:2000(E).

Stiffness

Figure 2B:
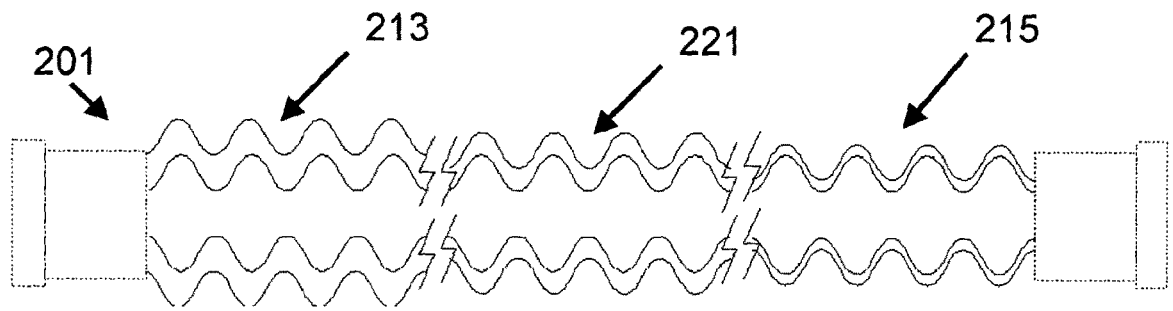

Referring again to FIG. 2A, preferably, a first region 213 of the conduit 203 adjacent the first opening 205 is stiffer than a second region 215 of the conduit 203 adjacent the second opening 207. Various embodiments include one or more additional regions between the first region 213 and the second region 215 having different stiffness characteristics than the first region 213 and the second region 215 (for example, stiffness characteristics intermediate those of the first region 213 and the second region 215). A three-region tube 201, for example, can impart a better curving profile in comparison to a two-region tube 201. A three-region tube 201 schematic is shown in FIG. 2B. This example comprises a third region 221 intermediate the first region 213 and the second region 215.

The first region 213 and/or the second region 215 can be an absolute distance, such as 5 cm or 10 cm (or about 5 cm or 10 cm). The first region 213 and/or the second region 215 can also represent a relative distance. In at least one embodiment, the first region 213 comprises 10-30% (or about 10-30%), or 30-50% (or about 30-50%), of the total length of the tube 201 (where for example, the total length of the tube 201 is the distance from the first opening 205 to the second opening 207, exclusive of cuffs or connectors 223 or any other separate terminal component attached to the end of the tube 201). For example, the first region 213 can comprise 33% (or about 33%), or 35% (or about 35%) of the total length of the tube 201 (where for example, the total length of the tube 201 is the distance from the first opening 205 to the second opening 207). In at least one embodiment, the second region 215 comprises 5-15% (or about 5-15%), or 15-50% (or about 15-50%), of the total length of the tube 201 (where for example, the total length of the tube 201 is the distance from the first opening 205 to the second opening 205). For example, the second region 215 thereof comprises 10% (or about 10%), or 15% (or about 15%) of the total length of the tube 201 (where for example, the total length of the tube 201 is the distance from the first opening 205 to the second opening 207). In at least one embodiment of a standard 1.8 m tube 201, the first region 213 is 0.3-0.7 m (or about 0.3-0.7 m) in length and preferably 0.5 m or thereabout, the second region 215 is 0.1-0.2 m (or about 0.1-0.2 m) in length and preferably 1.15 m or thereabout, and a third region 221 intermediate the first region 213 and second region 215 is between 1.0-1.5 m in length and preferably 0.15 m or thereabout. In any event, the first region 213 and second region 215 represent substantial lengths of the tube 201.

The difference in stiffness in these regions represents a significant departure from the prior art. A typical prior art delivery tube might incorporate an extruded corrugated conduit. At an extremely localised level, for example within the pitch of the corrugations, which is typically less than 1 cm, the stiffness of the conduit will vary. The corrugating process may result in a stiffer wall at the troughs of the corrugations than the peaks. However, between the two ends of the tube connectors, the stiffness properties across any substantial length are essentially the same as the properties of any other substantial length of the conduit. That is, these properties do not substantially vary at the macro level, as they do in the embodiments described herein.

Figure 3:
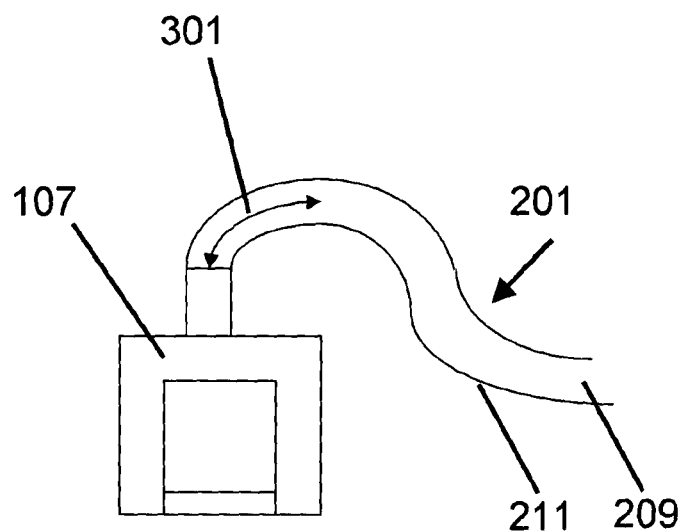
FIG. 3 shows a medical circuit demonstrating drain-back length of a tube.

Certain embodiments include the realization that the stiffness of the first region 213 can be defined in terms of a "drain-back length." As shown in FIG. 3, when the tube 201 is engaged with a humidifier 107 or other source of humidified gas, the tube 201 is generally upright at the point of engagement. In other words, the slope of a hypothetical line drawn through the center of the tube 201 is nearly infinite. Without some kind of support holding the tube 201 in this position, the flexibility of the tube 201 naturally causes it to bend at a distance away from the point of engagement. Thus, the slope of the hypothetical line through the center of the tube 201 gradually decreases as the distance from the point of engagement increases. At a certain distance away from the point of engagement, the slope of the hypothetical line reaches zero. After this distance, the slope of the hypothetical line gradually becomes more negative. When the slope of the hypothetical line is positive, condensate collecting on the tube's wall 211 surrounding the lumen 209 can theoretically "drain back" into the humidifier 107 under the force of gravity. Conversely, when the slope of the hypothetical line is negative, the condensate will theoretically drain away from the humidifier 107.

Thus, for an unsupported tube 201, the drain-back length 301 can be defined in terms of the distance between the point of connection to a humidifier 107 (or other source of humidity) and the point when the slope of the hypothetical line through the center of the tube 201 is zero. In general, the drain-back length 301 is the length of tube 201 measured from the point of connection to a humidifier 107 in which condensate collecting on the wall 211 surrounding the lumen 209 will naturally drain back into the humidifier 107. As the first region 213 becomes stiffer, the drain-back length 301 increases. If the first region 213 is less stiff, the drain-back length 301 decreases. In certain embodiments, the drain-back length 301 is 350-400 mm (or about 350-400 mm), e.g., 380 mm (or about 380 mm). A study was conducted to assess the effect of stiffness on the ability of the tube 201 to allow condensation on the tube wall 211 to drain back into the humidifier 107. A tube 201 with a thick cladding was connected to an AIRVO humidifier manufactured by Fisher & Paykel Healthcare Limited in Auckland, New Zealand. The drain-back length was measured to be 380 mm. In order to eliminate the insulating effect of the cladding and focus on the effect of drain-back length, a tube with no cladding was used. The drain-back length of 380 mm was replicated using a retort stand to hold the tube in place. The AIRVO humidifier was then turned on and run at a flow rate of 15 L/min. A small desk fan was placed 40 cm away from the humidifier outlet and turned on to the highest setting. This unrealistic draft condition was imposed to amplify possible condensation. Distal to the retort stand, the tube was allowed to assume a horizontal position lying on a desk. The AIRVO humidifier and fan were left running for 16 hours. After this time, the tube was removed from the AIRVO humidifier, and the tube was weighed.

By forming a tube 201 such that a significant length is oriented upward (or at least positively sloped) adjacent to the humidified gases delivery device, condensation forming in this portion of the tube 201 runs back into the humidified gases delivery device. Certain embodiments include the realization that forming the tube 201 with a suitable drain-back length 301 provides for this upward extension while obviating the need for a bulky or complex rigid connector. Referring again to FIG. 2A, several properties can affect the stiffness of the conduit 203. For example, in at least one embodiment, the fact that the conduit 203 is stiffer adjacent the first opening 205 than it is adjacent the second opening 207 results from the wall 211 of the conduit 203 being thicker adjacent the first opening 205 than it is adjacent the second opening 207. Preferably, the first region 213 has an average wall 211 thickness of 0.5-2.0 mm (or about 0.5-2.0 mm), or 1.0-2.0 mm (or about 1.0-2.0 mm), or 1.1-1.6 mm (or about 1.1-1.6 mm), or 1.6 mm (or about 1.6 mm), or 1.58 mm (or about 1.58 mm), or 1.18 mm (or about 1.18 mm). Preferably, the second region 215 has an average wall 211 thickness of 0.1-1.0 mm (or about 0.1-1.0 mm), or 0.1-0.7 mm (or about 0.1-0.7 mm), or 0.1-0.5 mm (or about 0.1-0.5 mm), or 0.2-0.7 mm (or about 0.2-0.7 mm), or 0.3-0.6 mm (or about 0.3-0.6 mm), or 0.30 mm (or about 0.30 mm), 0.33 mm (or about 0.33 mm), 0.37 mm (or about 0.37 mm), 0.50 mm (or about 0.50 mm), 0.53 mm (or about 0.53 mm), 0.54 mm (or about 0.54 mm), or 0.56 mm (or about 0.56 mm). A third region 211 intermediate the first region 213 and second region 215 can have an average wall 211 thickness of 0.5-1.0 mm (or about 0.5-1.0 mm), preferably 0.6 mm or thereabout. In certain embodiments, the average wall 211 thickness is at least 25% (or about 25%) greater, at least 100% (or about 100%) greater, or at least 200% (or about 200%) greater in the first region 213 than in the second region 215.

Another example measure of thickness is average thickness per unit length. Preferably, per unit length, the ratio of average wall 211 thickness in the first region 213 to the average wall 211 thickness in the second region 221 is 1.5:1-5.5:1 (or about 1.5:1-5.5:1), or 4.5:1-5.0:1 (or about 4.5:1-5.0:1), or 2.0:2.5 (or about 2.0:2.5). For an example corrugated tube 201, the ratio can be 4.8:1 (or about 4.8:1), measured at the crests, and 2.2:1 (or about 2.2:1), measured at the troughs.

In at least one embodiment, the fact that the conduit 203 is stiffer adjacent the first opening 205 than it is adjacent the second opening 207 results from the wall 211 of the conduit 203 having greater mass adjacent the first opening 207 than adjacent the second opening 207. Per unit length, the ratio of average wall 211 mass in the first region 213 to the average wall 211 mass of the tube 201 in the second region 215 can be 1.5:1-1.9:1 (or about 1.5:1-1.9:1), or 1.5:1-2:1 (or about 1.5:1-2:1). The first region 213 can have an average wall 211 mass of 50-110 g/m (or about 50-110 g/m), or 65-100 g/m (or about 65-100 g/m), or 65-80 g/m (or about 65-80 g/m), or 70 g/m (or about 70 g/m), or 75 g/m (or about 75 g/m). The second region 215 can have an average wall 211 mass of 20-50 g/m (or about 20-50 g/m), or 30-50 g/m (or about 30-50 g/m), or 30-45 g/m (or about 30-45 g/m), or 35-45 g/m (or about 35-45 g/m), or 40 g/m (or about 40 g/m), or 42 g/m (or about 42 g/m). A third region 221 intermediate the first region 213 and second region 215 can have an average wall 211 mass of 45-65 g/m (or about 45-65 g/m), preferably 50 g/m or thereabout. In certain embodiments, the average wall 211 mass is at least 25% (or about 25%) greater, at least 100% (or about 100%) greater, or at least 200% (or about 200%) greater in the first region 213 than in the second region 215.

In at least one embodiment, the fact that the conduit 203 is stiffer adjacent the first opening 205 than it is adjacent the second opening 207 results from the wall 211 of the conduit 203 having greater volume adjacent the first opening 207 than adjacent the second opening 207. Per unit length, the ratio of average wall 211 volume in the first region 213 to the average wall 211 volume in the second region 215 can be 1.5:1-3.5:1 (or about 1.5:1-3.5:1), or 2.0:1-3.0:1 (or about 2.0:1-3.0:1), or 2.5:1-2.6:1 (or about 2.5:1-2.6:1). The first region 213 can have an average wall 211 volume of 1.0-2.0 cm3/cm (or about 1.0-2.0 cm3/cm), or 1.0-1.5 cm3/cm (or about 1.0-1.5 cm3/cm), or 1.20 cm3/cm (or about 1.20 cm3/cm), or 1.17 cm3/cm (or about cm3/cm). The second region 215 can have an average wall 211 volume of 0.2-1.0 cm3/cm (or about 0.2-1.0 cm3/cm), or 0.40-0.55 cm3/cm (or about 0.40-0.55 cm3/cm), or 0.45 cm3/cm (or about 0.45 cm3/cm), or 0.50 cm3/cm (or about 0.50 cm3/cm). In certain embodiments, the average wall 211 volume is at least 25% (or about 25%) greater, at least 100% (or about 100%) greater, or at least 200% (or about 200%) greater in the first region 213 than in the second region 215.

In at least one embodiment, the fact that the conduit 203 is stiffer adjacent the first opening 205 than it is adjacent the second opening 207 results from the wall 211 having a greater flex modulus adjacent the first opening 205 than adjacent the second opening 207.

FIG. 4A-4E illustrates test equipment for measuring the flex modulus of tubes. The illustrated equipment comprises a commercially-available Instron machine.

Figure 4A:
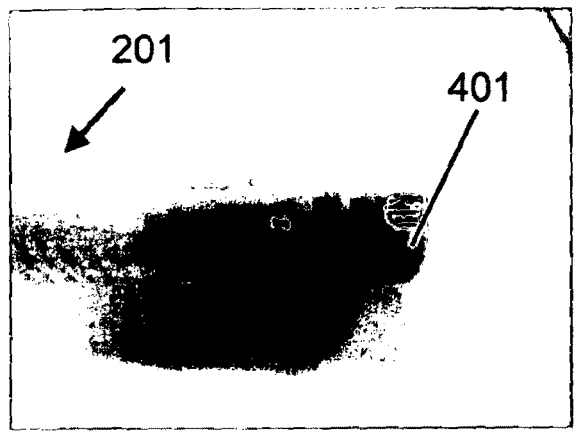

As shown in FIG. 4A, for testing a tube 201, a plug 401 is inserted into an opening of the tube 201 sample.

Figure 4B:
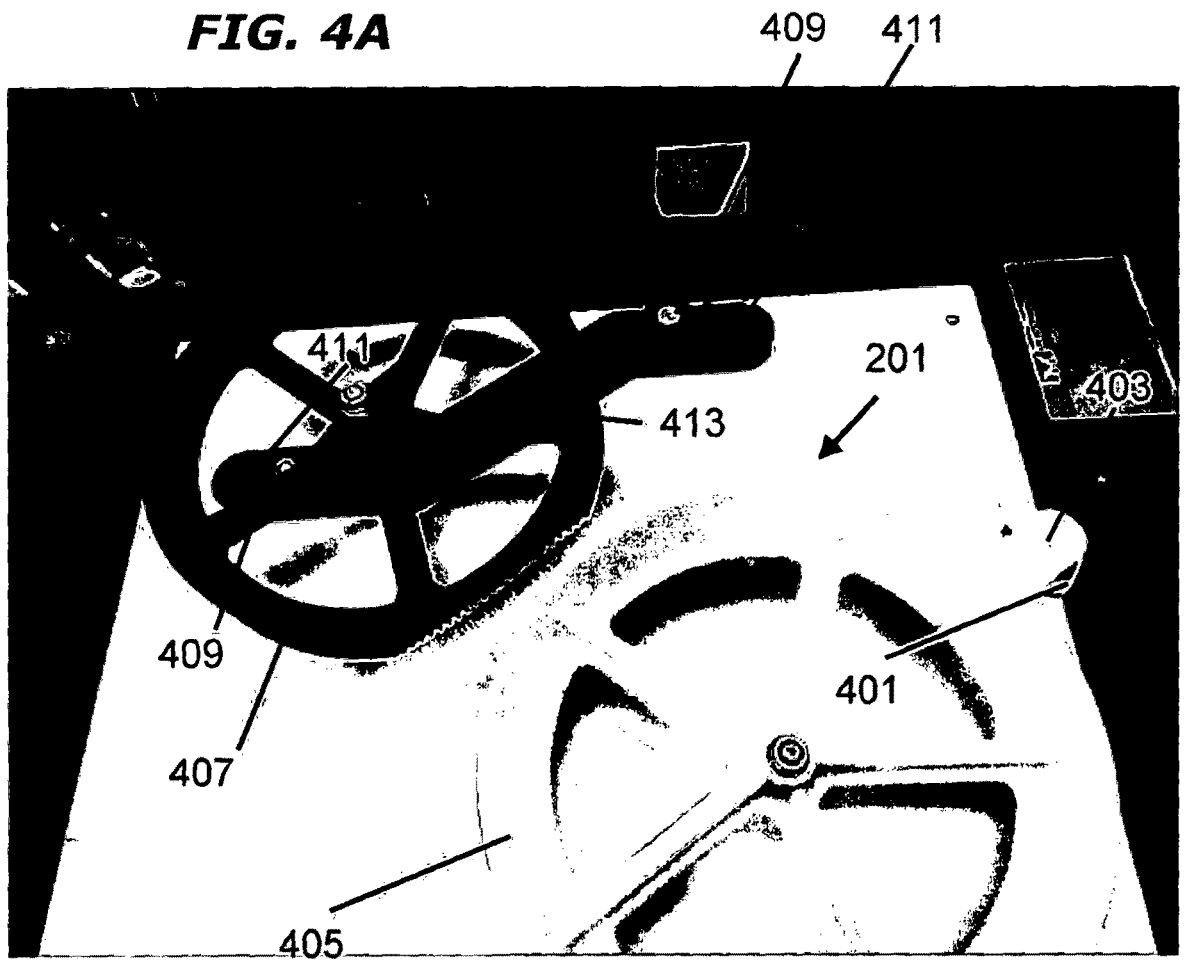

As shown in FIG. 4B, the plug 401 is connected to an arm 403 of test wheel 405. The tube 201 is wrapped around the test wheel 405 (which has a diameter of 78 mm) and is secured by a support wheel 407 which has a diameter of 75 mm. The support wheel 407 touches the tube 201 in order to secure its position. It does not crush the tube 201 sample. The location of support wheel 407 is adjusted accordingly by adjusting the position of screws 409 along slots 411 in the supporting frame 413 for the support wheel 407.

As shown in FIG. 4C, a cord 415 attached to the test wheel 405. Starting from a point where the arm 403 of the test wheel 405 is adjacent the support wheel 407 and the tube 201 is in an unflexed condition, the cord 415 is then pulled at a constant rate of 250 mm per minute for a distance of 100 mm. The tensile load on the cord 415 is recorded as a function of distance.

The test is repeated with the tube 201 rotated to each of four orientations about the tube axis (shown in FIGS. 4D and 4E) to account for asymmetries in the form of the tube 201. Testing according to this procedure provides flexure property data for the tube 201. Testing a tube 201 with potentially different flex moduli at locations along the tube 201 comprises testing each region of the tube 201 by cutting out the region, mounting the region, and testing according to this procedure.

Figure 5A:
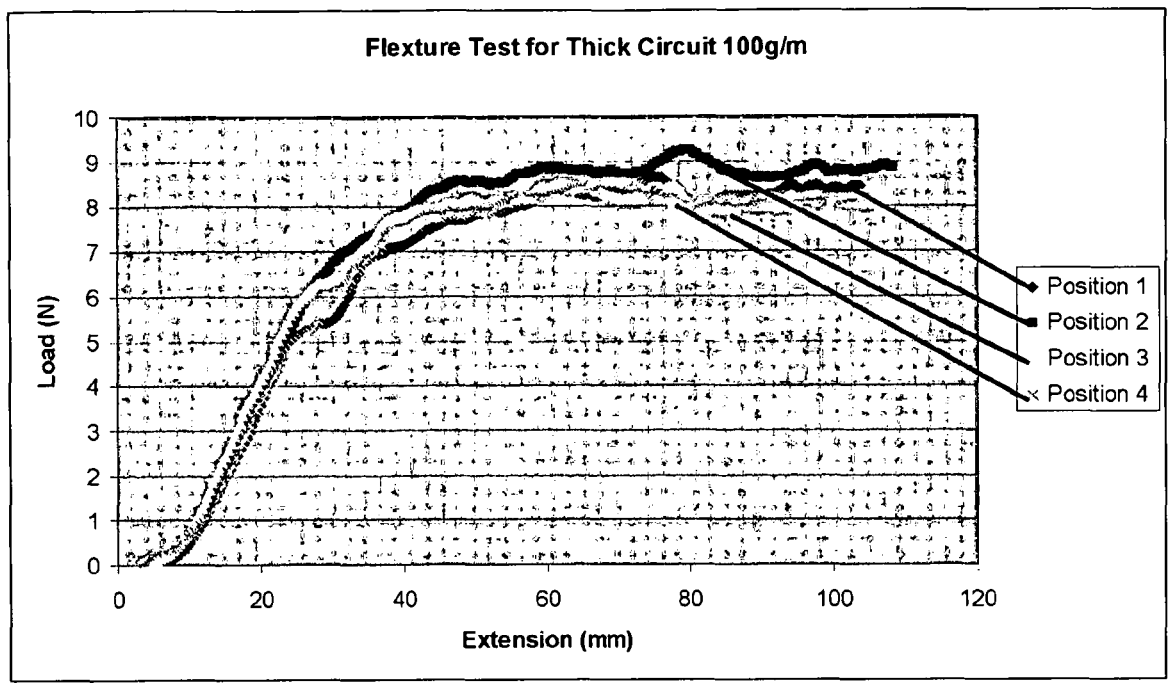
FIG. 5A is a chart plotting test results for a tube sample having 100 g/m mass.
Figure 5B:
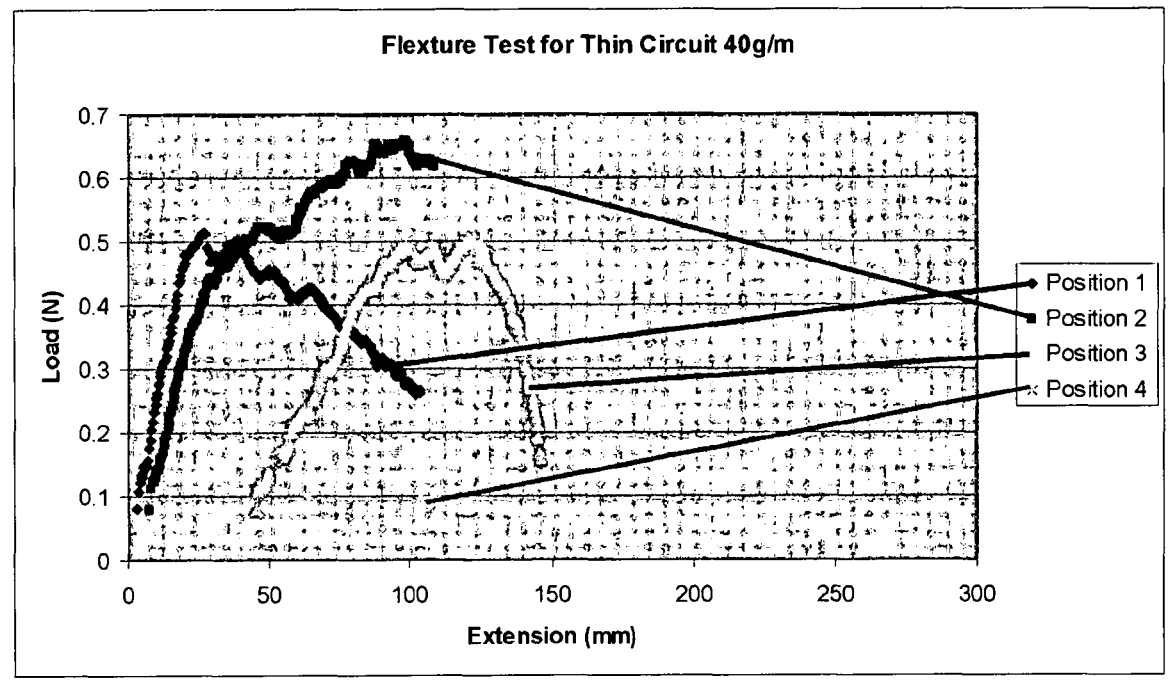
FIG. 5B is a chart plotting test results for a tube sample having 40 g/m mass.

For a tested section, the flex modulus is calculated as the gradient of the linear portion of the load versus extension plot created through the test. The flex modulus for the test section is the average flex modulus calculated for each of the four orientations. By way of example, FIG. 5A illustrates flexure test data for the four orientations of a section of corrugated tube having a tube weight of 100 g/m; FIG. 5B illustrates flexure test data for the four orientations of a section of corrugated tube having a tube weight of 40 g/m.

Figure 5C:
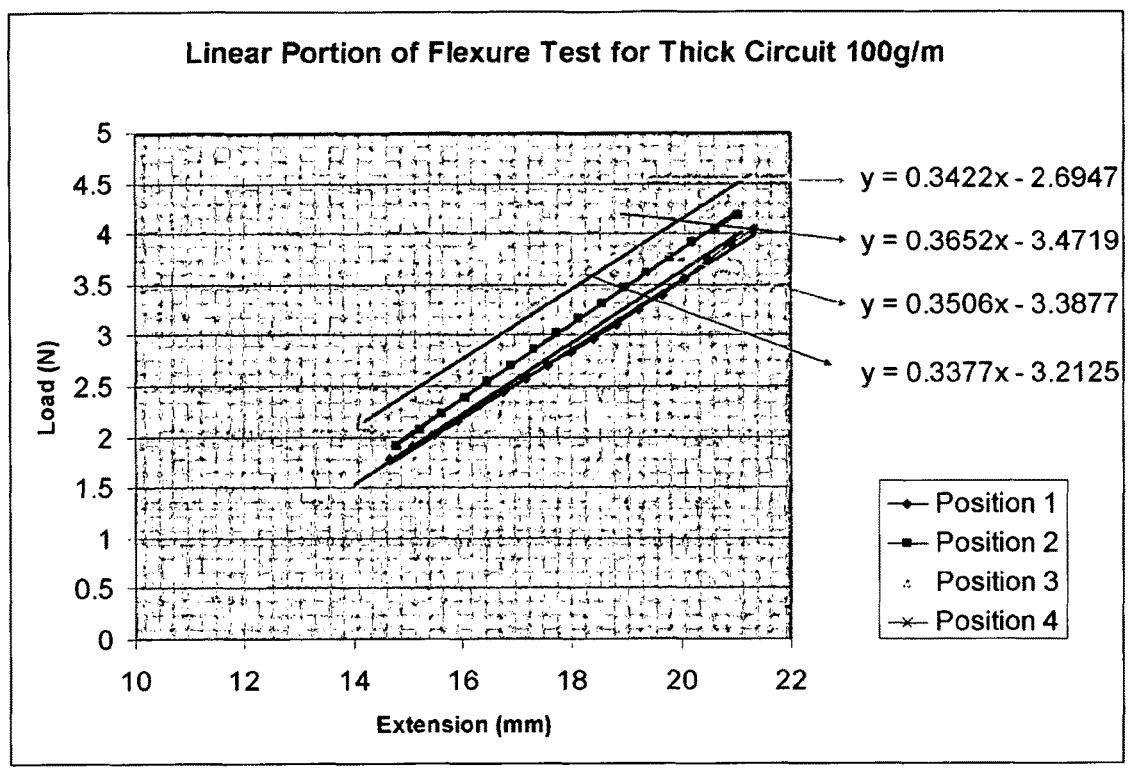
FIG. 5C is an enlarged plot of the linear portion of the flexure text plots of FIG. 5A.

FIG. 5C illustrates only the linear portion of the plots of FIG. 5A, with lines of best fit for each orientation of the tube. The line of best fit for the tube in a first orientation and has a gradient of 0.3377 N/mm. The line of best fit for the tube for a second orientation has a gradient of 0.3652 N/mm. The line of best fit for the tube in the third orientation has a gradient of 0.342 N/mm. The line of best fit for the tube oriented in the fourth position and has a gradient of 0.3506 N/mm. The average gradient, and therefore the flex modulus according to this test calculated for this tube portion is 0.3488 N/mm.

Figure 5D:
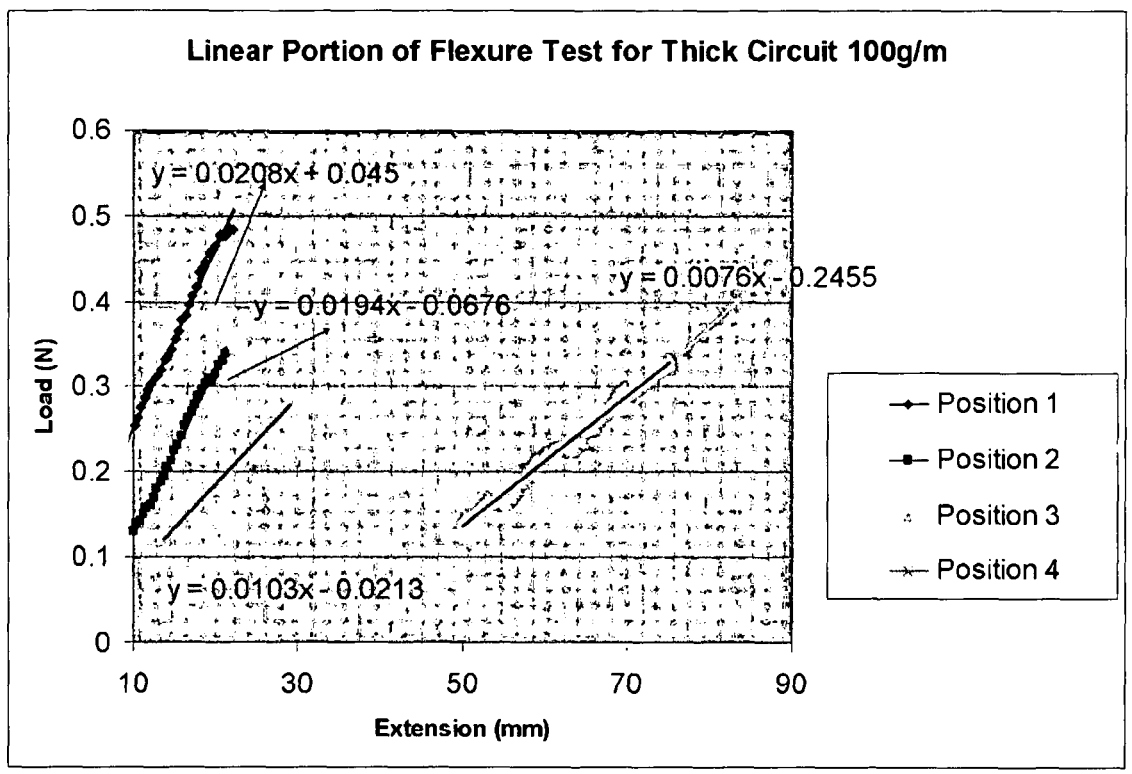
FIG. 5D is an enlarged plot of the linear portion of the flexure text plots of FIG. 5B.

FIG. 5D illustrates an enlarged part of the curves in FIG. 5B, with lines of best fit for each orientation of the tube. The line of best fit for the tube in a first orientation has a gradient of 0.0208 N/mm. The line of best fit for the tube in a second orientation has a gradient of 0.0194 N/mm. The line of best fit for the tube in a third orientation has a gradient of 0.0076 N/mm. The line of best fit for the tube oriented in a fourth orientation has a gradient of 0.0103 N/mm. The average gradient, and therefore the flex modulus measured according to this test calculated for this tube portion is 0.01452 N/mm.

From these tests, it can be seen that the portion of corrugated tube having a tube weight of 40 g/m has a test flex modulus of about 0.015 N/mm, while the portion of corrugated tube having a tube weight of 100 g/m has a test flex modulus of 0.349 N/mm. Thus, the flex modulus of the 100 g/m sample is more than 20 times the flex modulus of the 40 g/m tube.

Per unit length, the ratio of flex modulus in the first region to that in the second region, as defined by the foregoing test method, can be 10:1-250:1 (or about 10:1-250:1), 100:1-220:1 (or about 100:1-220:1), or 170:1-200:1 (or about 170:1-200:1), or 188:1 (or about 188:1), or 185:1 (or about 185:1). In certain embodiments, the average flex modulus is at least 25% (or about 25% greater), at least 100% greater, or at least 200% greater in the first region than in the second region.

Wall Composition

In at least one embodiment, the wall is formed from an extrudate comprising one or more polymers. Preferred polymers include Linear Low Density Polyethylene (LLDPE), Low Density Polyethylene (LDPE), Polypropylene (PP), Polyolefin Plastomer (POP), Ethylene Vinyl Acetate (EVA), Plasticized Polyvinylchloride (PVC), or a blend of two or more of these materials. The polymer(s) forms at least 98.4 (or about 98.4), 98.5 (or about 98.5), 98.6 (or about 98.6), 98.7 (or about 98.7), 98.8 (or about 98.8), 98.9 (or about 98.9), 99.0 (or about 99.0), 99.1 (or about 99.1), 99.2 (or about 99.2), 99.3 (or about 99.), 99.4 (or about 99.4), 99.5 (or about 99.5), 99.6 (or about 99.6), 99.7 (or about 99.7), 99.8 (or about 99.8), or 99.9 (or about 99.9) weight percent (wt. %) of the total extrudate. In particular embodiments, the extrudate comprises 99.488 (or about 99.488) wt. % or about 99.49 (or about 99.49) wt. % LLDPE.

The extrudate can also optionally comprise one or more surface-modifying agents. A surface-modifying agent is an additive that, either alone or in combination with another substance, affects the properties of a material's surface. Such an agent can assist in increasing the surface energy (or the wettability) of the wall surface. Increasing the surface energy can advantageously promote reduced contact angles between drops or beads of condensate or liquid that may build up on the surface. Specifically, a drop or bead may be spread across a larger surface area of the wall and, therefore, be more likely to re-evaporate into the gas stream flowing through the lumen.

Including a surface-modifying agent can be particularly advantageous in corrugated tubes. In a corrugated tube, a droplet or bead of condensate is more likely to form in a part of the corrugation of low temperature position. The low temperature position is typically a part of the corrugation closest to or most exposed to ambient conditions surrounding the tube. Altering the surface properties of the tube wall can allow a droplet or bead formed at the low temperature position to spread across the tube surface and, in doing so, move toward a region of warmer temperature. Such migration of movement of the droplet or bead can allow for improved re-evaporation rates, both due to the droplet moving toward regions of warmer temperatures, as well as toward regions of the tube which are exposed to greater or faster gas stream flows.

Suitable surface modifying agents include glycerol monostearate (GMS), ethoxylated amine, alkanesulphonate sodium salt, and lauric diethanolamide and additives comprising these substances. MLDNA-418 supplied by Clariant (New Zealand) Ltd. and under the product name "418 LD Masterbatch Antistatic" is a surface modification agent master batch with 5(±0.25) % glycerol monostearate (CAS No. 123-94-4) as an active ingredient. Preferably the surface modifying agent comprises at least about 0.05 (or about 0.05), 0.1 (or about 0.1), 0.15 (or about 0.15), 0.2 (or about 0.2), 0.25 (or about 0.25), 0.3 (or about 0.3), 0.35 (or about 0.35), 0.4 (or about 0.4), 0.45 (or about 0.45), 0.5 (or about 0.5), 1.1 (or about 1.1), 1.2 (or about 1.2), 1.3 (or about 1.3), 1.4 (or about 1.4), or 1.5 (or about 1.5) wt. % of the total extrudate. For example, in at least one embodiment, the extrudate comprises 0.25 wt. % (or about 0.25 wt. %) of surface modifying agent. As another example, in at least one embodiment, the extrudate comprises 0.5 wt. % (or about 0.5 wt. %) of surface modifying agent.

Other methods can also be used to increase surface energy and reduce contact angle. Suitable methods include physical, chemical, and radiation methods. Physical methods include, for example, physical adsorption and Langmuir-Blodgett films. Chemical methods include oxidation by strong acids, ozone treatment, chemisorption, and flame treatment. Radiation methods include plasma (glow discharge), corona discharge, photo-activation (UV), laser, ion beam, electron beam, and gamma irradiation.

By selecting a suitable surface modification method or agent, it is possible to provide a conduit wall having surface property contact angles of less than 50 (or about 50), 45 (or about 45), 40 (or about 40), 35 (or about 35), 30 (or about 30), 25 (or about 25), 20 (or about 20) degrees (°), as measurable by an angle measurement device such as a geniometer. For instance, tube walls having surface property contact angles of less than 35° (or about 35°) provide useful results.

TABLE 1 below shows contact angle measurements for various LLDPE samples, including a sample treated with a surface-modifying agent and a sample treated with radiation. The contact angle measurements were based on static drop shape testing methods conducted in accordance with ASTM Standard D7334, 2008, "Standard Practice for Surface Wettability of Coatings, Substrates and Pigments by Advancing Contact Angle Measurement."

TABLE 1

| Description of Surface | Liquid | Average Contact Angle (degrees) |
|---|---|---|
| Linear Low-density Polyethylene (LLDPE), as manufactured | Water | 97.39 |
| Linear Low-density Polyethylene (LLDPE), fluorinated, washed | Water | 67.56 |
| Linear Low-density Polyethylene (LLDPE), plasma-treated, 10% O2, 300 Watts, 30 seconds | Water | 44.98 |

TABLE 1-continued

| Description of Surface | Liquid | Average Contact Angle (degrees) |
|---|---|---|
| Linear Low-density Polyethylene (LLDPE), with 5% MLDNA-418 as surface modification agent additive | Water | 33.09 |

The sample with 5% MLDNA-418 surface modifying agent produced the lowest measured contact angle compared to other surface modification methods tested.

Foam

The tube wall described above can be formed from polymer foam in certain embodiments. Foam is a solid material having gas voids dispersed throughout. The voids can be open cell or reticulated (such that a majority, e.g., 51-100%, of the voids interconnect with other voids). The voids can also be closed cell so that most (e.g., 80%, 90%, or more) of the cells do not interconnect with other voids. Foams with open-cell voids can be advantageous because they are generally less dense, require less material, and consequently are less expensive to produce than foam with closed-cell voids. Preferably, however, the voids are closed cell, which improves and better controls the insulating properties of the wall. Foams with closed-cell voids can have the additional advantage of being easier to manufacture than foams with open-cell voids.

In embodiments comprising a foam wall, the foam wall is preferably a single piece of polymer foam, for example being formed by extrusion of a single extrudate.

A foam wall can advantageously provide an improved level of thermal insulation for the lumen, compared with the level of thermal insulation provided by a non-foam wall. Thus, in at least one embodiment, the wall is thermally insulative of the contents (such as for example humidified gases flowing through the gas flow passage) of the elongate conduit to the potential cooling effects of the environment surrounding the medical tube (for example, insulating from the ambient air surrounding a breathing circuit, or a laparoscopic insufflation system). The environment surrounding the medical tube is for example, a hospital ward or room, an operating theater, a home bedroom, or other locations where the patient may be located.

In various embodiments, a foam wall has or provides for a thermal conductivity of 0.2-0.4 W/m-K (Watts per meter Kelvin) (or about 0.2-0.4 W/m-K). It will be appreciated, however, that a foam wall can beneficially provide for other levels of thermal conductivity, and thermal conductivities of 0.15-0.35 W/m-K (or about 0.15-0.35 W/m-K) or 0.25-0.45 W/m-K (W/m-K) are also contemplated.

An example method for forming a foam wall includes the addition of a chemical foaming agent to the extrudate. Chemical foaming agents are sometimes also referred to as blowing agents. A chemical foaming agent enables foaming of the extrudate material as part of or after the extrusion process, which is explained in greater detail below. The chemical foaming agent can comprise at least 0.005 (or about 0.005), 0.006 (or about 0.006), 0.007 (or about 0.007), 0.008 (or about 0.008), 0.009 (or about 0.009), 0.01 (or about 0.10), 0.011 (or about 0.011), 0.012 (or about 0.012), 0.013 (or about 0.013), 0.014 (or about 0.014), 0.015 (or about 0.015), 0.016 (or about 0.016), 0.017 (or about 0.017), 0.018 (or about 0.018), 0.019 (or about 0.019), or 0.02 (or about 0.02) wt. % of the total extrudate. For example, the chemical foaming agent can comprise 0.01-0.012 (or about 0.01-0.012) wt. % of the total extrudate. As part of a chemical foaming extrusion process, the polymer component of an extrudate is mixed with a chemical foaming agent.

Some preferred chemical foaming agents comprise calcium oxide. For example, MHYNA-CF20E supplied by Clariant (New Zealand) Ltd. under the product name Hydrocerol CF20E is a chemical foaming agent in the form of a blowing agent master batch with about 0.5-1% calcium oxide as an active ingredient.

During a chemical foam extrusion process the polymer resin component and chemical foaming agent(s) are mixed and melted. The chemical foaming agent(s) decomposes and liberates gas which is dispersed in the polymer (or master batch or extrudate) melt and which expands upon exiting the die of an extruder.

It will also be appreciated other foaming techniques can be employed for forming a foam wall, such as by physical rather than chemical foaming methods. Physical foaming methods include gas being introduced directly into the extrudate while under pressure. As the extrudate is extruded, the pressure is reduced allowing the gas to expand. For example, one such physical foaming technique includes blowing or injecting of gas(es) into the extrudate at or near the point of extrusion. Such gas(es) may include nitrogen, carbon dioxide, pentane or butane.

Sheath

Figure 2C:
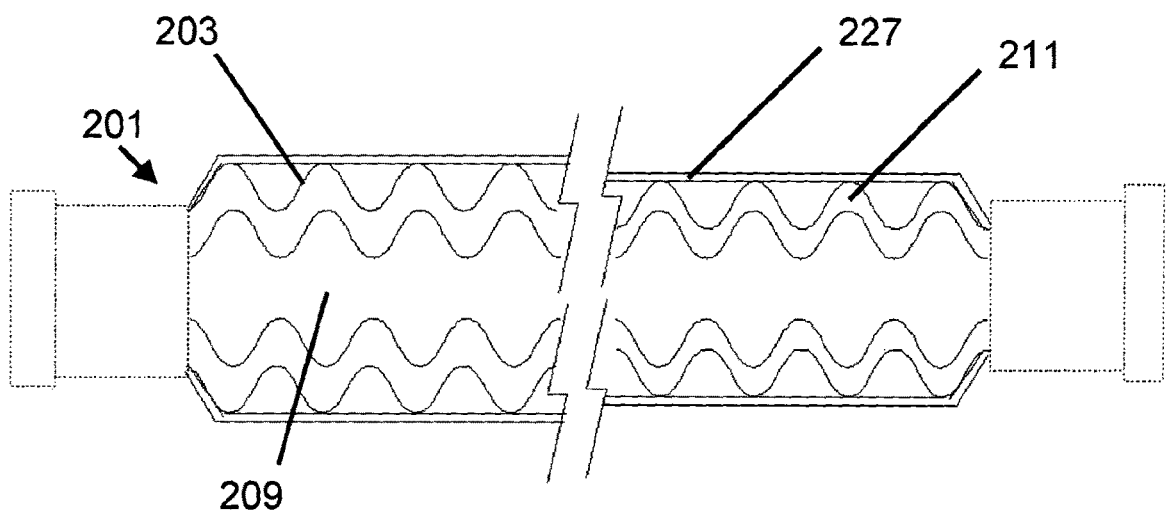

In certain embodiments, the elongate conduit 203 can further comprise a sheath 227, as shown in FIG. 2C. A sheath 227 is a member partially or fully surrounding the wall 211. The sheath 225 can be secured to the wall 211 of the conduit 203 at locations along the wall 211 or may be secured only to ends of the tube 201. The sheath 227 can be used to secure conductive filaments (described below) in place and/or to prevent heat loss due to cool air currents impinging on the tube wall 211.

Although the sheath 227 can be incorporated into a conduit 203 comprising a smooth wall (not shown) or a corrugated wall 211, it can be particularly advantageous to include such a sheath 227 with a corrugated wall. The sheath can trap air between adjacent outer crests (or annular protrusions) of the corrugations. This may assist in further insulation of the gas passing through the lumen 209.

For delivery tubes incorporating a sheath 227, the sheath 227 may be applied about wall 211 as an extruded outer layer, as a wrapping about the wall 211, or as a sleeve that is slid or pulled into position about the wall 211. Such a sheath 227 may be formed of similar materials as the wall 211 (described above), for example LLDPE. The sheath 227 may assist in further improving thermal performance of tube 201.

The sheath 227 may be of any necessary thickness, although thickness and the material used should be balanced with the need to maintain flexibility of the conduit 203. In one embodiment, it is contemplated the sheath 227 may have an average wall thickness of 100 microns (or about 100 microns).

However, the average thickness per unit length, average mass per unit length, average volume per unit length, or flex modulus can vary at the macro level along the length of the sheath 227. In some embodiments, the property measure can be greater at one region of the sheath 227 adjacent one end of the tube 201 than a region of the sheath 227 adjacent the other end. In other embodiments, the property measure may vary gradually along the length of the sheath 227. In other embodiments, the property measure may have distinct transitions moving along the length of the sheath 227. In some embodiments, the measure or characteristic may be greater at a region adjacent one end of the tube 201 than in a region at the mid-length portion of the tube 201 and may be greater at a region adjacent the other end of the tube 201 than at a region at the mid-portion of the tube 201.

For instance, the external sheath 227 can be thicker at the humidifier end of the tube 201 to better insulate the tube 201 and prevent heat loss where most of the condensation is likely to occur. A thicker sheath 227 at the humidifier end can also add to the stiffness of the tube 201 so it maintains a more vertical position for a greater distance, before bending toward the horizontal, thereby increasing drain-back length (not shown). In this way, more condensation is returned to the humidifier (not shown), rather than entering the breathing tube 201. A thinner sheath 227 at the patient end can increase flexibility and reduce weight to improve the comfort of the user.

Where a sheath 227 is extruded about the wall 211, for example, such an extrusion could be a sequential step to initial extrusion of the wall 211, that is, an extrusion step post-formation of the wall 211. Further, where an outer sheath 227, for example, is a wrap about the wall 211, the sheath 227 may be constructed in place from a tape or ribbon spirally wound about the length of the wall 211. Still further, where an outer sheath 227 is pre-formed as a hollow tube, it may be sleeved into position about the outside of the wall 211.

Conductive Filaments

In certain embodiments, a tube 201 can further comprise one or more conductive filaments. These conductive filaments may be heating filaments and/or sensing filaments.

Figure 6:
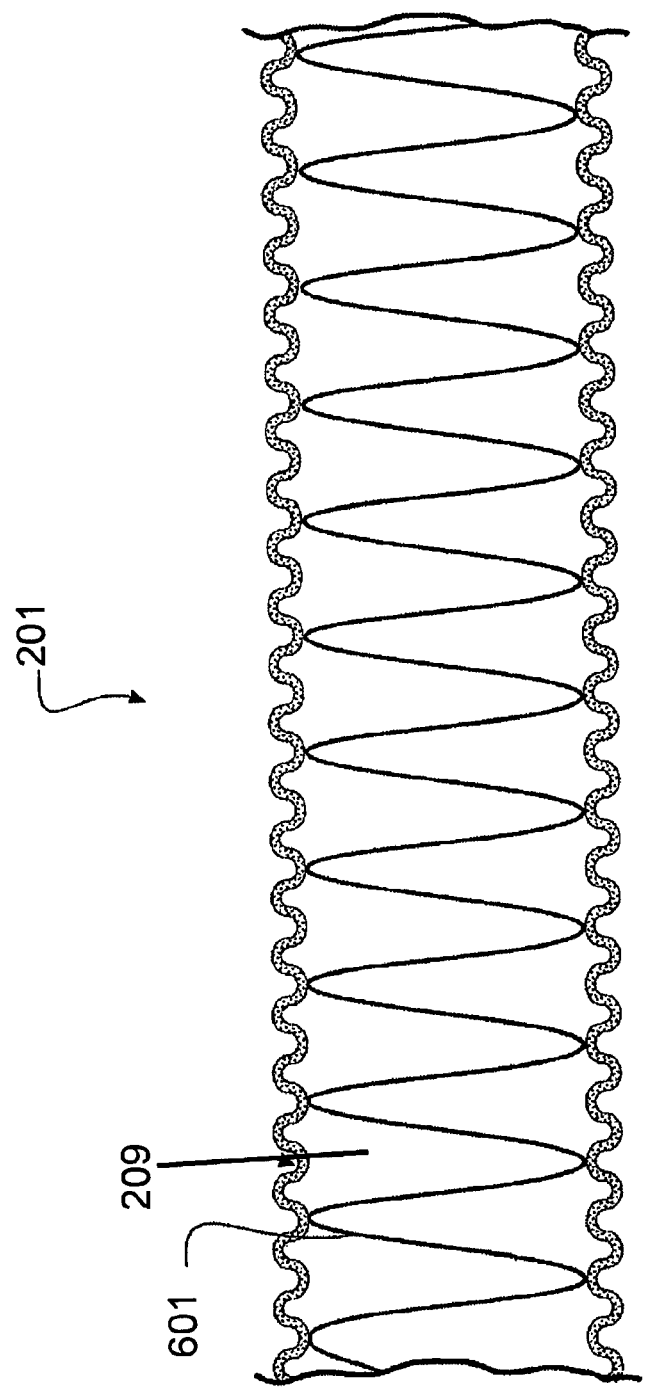
FIGS. 6-7 illustrate example placements of a heater wire.
Figure 7:
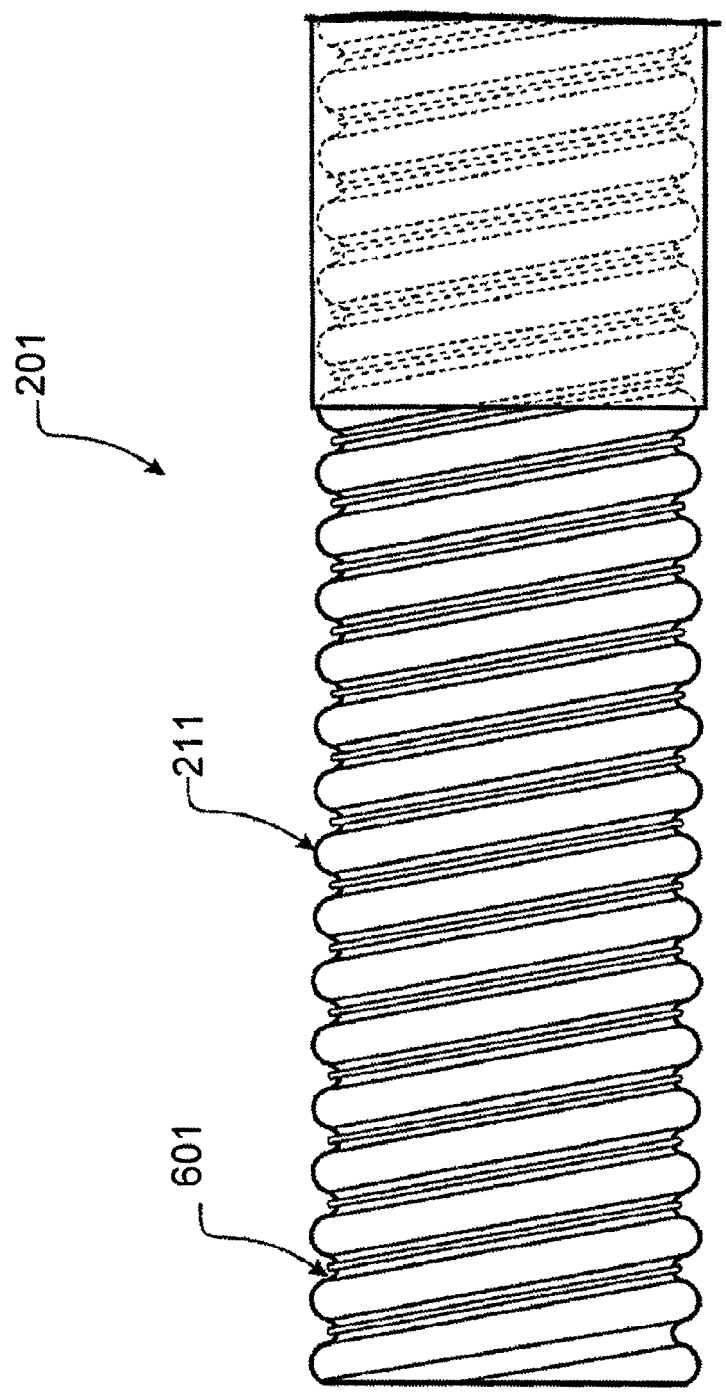

A filament can, for example, take the form of a wire or tape on or in the wall of the conduit. FIG. 6 illustrates an example placement of a heater wire 601 within the lumen 209 of a tube 201. Although the filament can be within the lumen 209, it can be desirable to move the filament out of the gas flow path. For example, the filament can be placed on the wall radially opposite the lumen or inside the wall. FIG. 7 illustrates the placement of a heater wire 601 about the external surface of the wall 211. Such placement can reduce the risk of ignition in an oxygen-rich gas flow and also improve laminar gas flow.

Materials for such filaments are conductive metals including copper or aluminum, or a PTC (positive temperature coefficient) type material. Aluminum is not as conductive as copper, but may be an economical choice even though the wire diameter is larger for the same resistance. While the applied circuit voltage is intrinsically safe (less than 50V), for corrosion resistance and electrical safety in the event of the wall or sheath being damaged, the wire will ideally be self-insulated, either by enamel coating, or anodizing in the case of aluminum.

In certain embodiments, a filament can be placed on the outer surface of the wall 211 (radially outward from the lumen 209), and a plastic sheath 227 can be fitted about the filament. In such a configuration, the sheath 227 can help to restrain the filament in position. Moreover, the sheath can also be included when the filament is placed in the lumen 209 or in the wall 211. As explained above, an insulating external sheath 227 prevents heat loss. However, the outer sheath 227 may be employed, regardless of whether a filament is also included.

Comparison with Uniform-Stiffness Tubes

Figure 8:
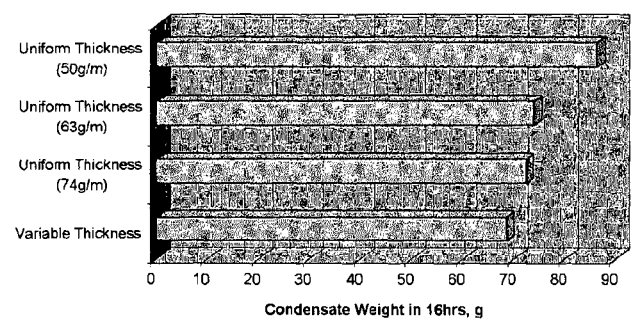
FIG. 8 is a plot comparing the condensate accumulation in uniform-stiffness tubes to that in a variable-stiffness tube.

FIG. 8 compares the condensate accumulation in uniform-stiffness tubes to that in a variable-stiffness tube. In this experiment, three uniform-stiffness tubes and one variable-stiffness tube were connected in circuit with sources of humidified gas and placed in a test chamber with a cooling flow of air simulating a typical hospital ward with conditioned air flowing over the circuit. The condensate that accumulated over a 16-hour period was collected and weighed. The results indicated the increasing the mass of the wall in the uniform-thickness tubes from 50 g/m to 63 g/m to 74 g/m reduced condensate accumulation. The variable-stiffness tube, made from three sections having a mass of 74 g/m at the first end, 63 g/m in an intermediate region, and 50 g/m at the second end, unexpectedly accumulated even less condensate than the 74 g/m tube.

One explanation for the unexpectedly improved performance of the variable-stiffness tube over the stiffest uniform-thickness tube may be the interaction with the humidifier that served as the source of humidified gas. The MR850 Humidifier, manufactured by Fisher & Paykel Healthcare Limited of Auckland, New Zealand, detects the patient-end temperature and controls the heater plate under the chamber and heating filament in the tube. The algorithm used by the humidifier involves putting gas into a tube, fully saturated, at 37° C., then heating the tube so that the temperature sensed at the end of the tube measures 40° C. Because the 50/63/74 g/m variable-stiffness tube has a relatively thin wall at the patient end, the temperature is lower at the patient end than it is at the patient end of the 74 g/m uniform-wall tube. Thus, the humidifier's control algorithm puts more power into the heater plate and heating filament with the variable-stiffness sample, resulting in less condensation at the humidifier-end of the tube.

Component in Medical Circuits

Figure 9:
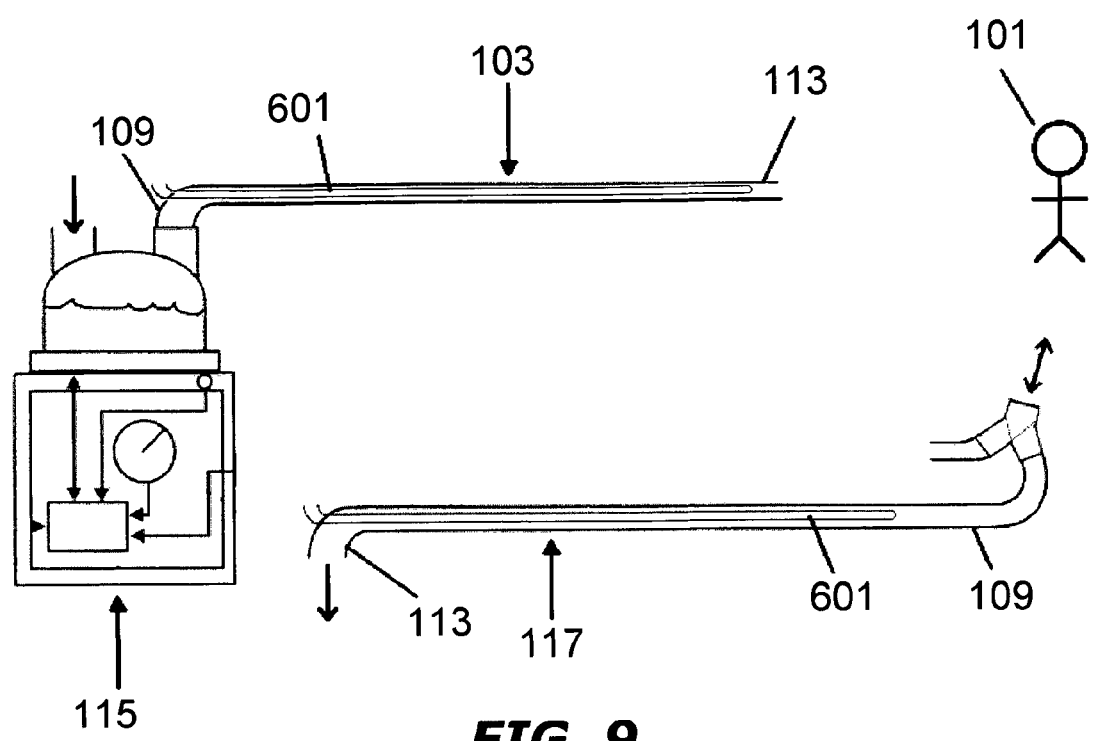
FIG. 9 shows an example medical circuit according to at least one embodiment.

Reference is next made to FIG. 9, which shows an example medical circuit according to at least one embodiment. The circuit comprises a variable-stiffness tube as described above for the inspiratory tube 103. The properties of the inspiratory tube 103 are similar to the tubes described above. The inspiratory tube 103 has an inlet 109, communicating with a source of humidified gas 115, and an outlet 113, through which humidified gases are provided to the patient 101. As described above, heater wires 601 can be placed within the inspiratory tube 103 to reduce the risk of rain out in the tubes by maintaining the tube wall temperature above the dew point temperature.

In FIG. 9, an expiratory tube 117 is also provided. The expiratory tube 117 also has an inlet 109, which receives exhaled humidified gases from the patient, and an outlet 113. As described above with respect to FIG. 1, the outlet 113 of the expiratory tube 117 can vent exhaled gases to the atmosphere, to the ventilator/blower unit 115, to an air scrubber/filter (not shown), or to any other suitable location.

The expiratory tube is optional, however. Inspiratory tubes 103 according to the above-described embodiments can be used with other forms of respiratory support, for example using a standalone blower humidifier without an expiratory return path. Examples of such products include the humidified CPAP delivery products and COPD therapy products of Fisher & Paykel Healthcare Limited of Auckland, New Zealand. In these systems, a combined blower/humidifier supplies humidified gases to the connected delivery tube. The delivery tube supplies these gases to a patient interface connected to the patient end of the delivery tube. The patient interface is typically a full face mask, nasal mask, nasal pillows for CPAP therapy, nasal prongs or nasal cannula for COPD therapy or a tracheal connector of an intubated patient where the device may be used to assist a transition off full ventilation.

Component of an Insufflation System

Laparoscopic surgery, also called minimally invasive surgery (MIS), or keyhole surgery, is a modern surgical technique in which operations in the abdomen are performed through small incisions (usually 0.5 to 1.5 cm) as compared to larger incisions needed in traditional surgical procedures. Laparoscopic surgery includes operations within the abdominal or pelvic cavities. During laparoscopic surgery with insufflation, it may be desirable for the insufflation gas (commonly CO2) to be humidified before being passed into the abdominal cavity. This can help prevent "drying out" of the patient's internal organs, and can decrease the amount of time needed for recovery from surgery. Insufflation systems generally comprise humidifier chambers that hold a quantity of water within them. The humidifier generally includes a heater plate that heats the water to create a water vapour that is transmitted into the incoming gases to humidify the gases. The gases are transported out of the humidifier with the water vapor.

Figure 10:
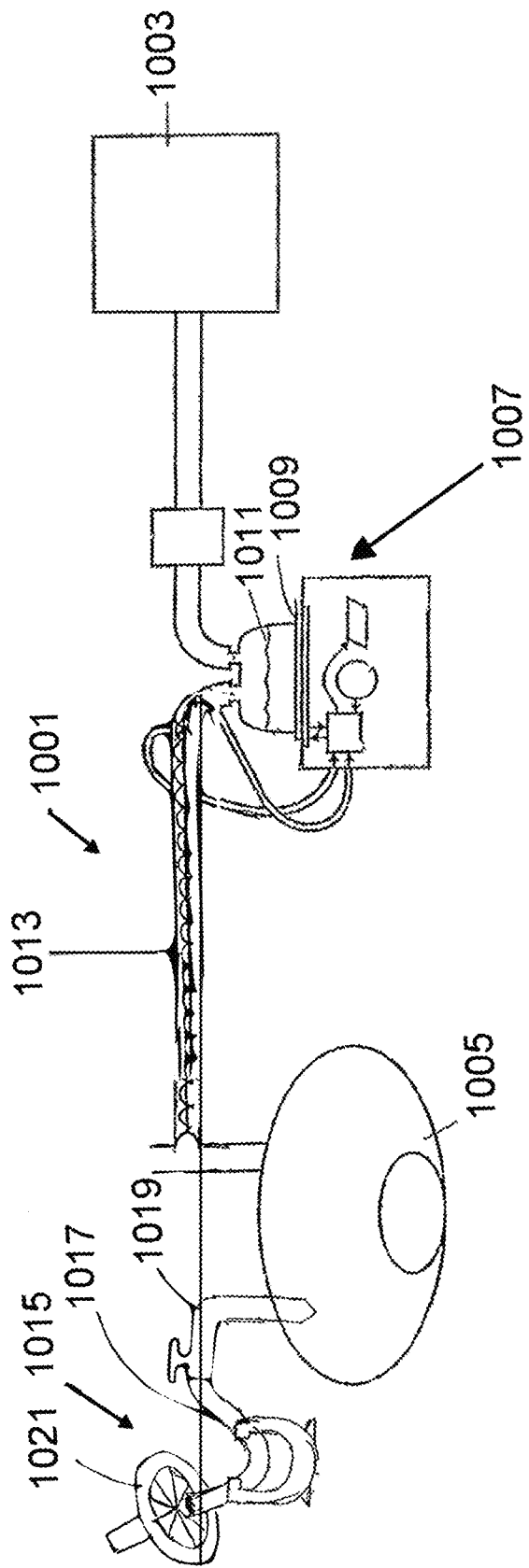
FIG. 10 shows an insufflation system according to at least one embodiment.

Reference is next made to FIG. 10, which shows an insufflation system 1001, according to at least one embodiment. The insufflation system 1001 includes an insufflator 1003 that produces a stream of insufflation gases at a pressure above atmospheric for delivery into the patient 1005 abdominal or peritoneal cavity. The gases pass into a humidifier 1007, including a heater base 1009 and humidifier chamber 1011, with the chamber 1011 in use in contact with the heater base 1009 so that the heater base 1009 provides heat to the chamber 1011. In the humidifier 1007, the insufflation gases are passed through the chamber 1011 so that they become humidified to an appropriate level of moisture.

The system 1001 includes a delivery conduit 1013 that connects between the humidifier chamber 1011 and the patient 1005 peritoneal cavity or surgical site. The conduit 1013 is a variable-stiffness tube as described above. The conduit 1013 has a first end and second end, the first end being connected to the outlet of the humidifier chamber 1011 and receiving humidified gases from the chamber 1011. The second end of the conduit 1013 is placed in the patient 1005 surgical site or peritoneal cavity and humidified insufflation gases travel from the chamber 1011, through the conduit 1013 and into the surgical site to insufflate and expand the surgical site or peritoneal cavity. The system also includes a controller (not shown) that regulates the amount of humidity supplied to the gases by controlling the power supplied to the heater base 1009. The controller can also be used to monitor water in the humidifier chamber 1011. A smoke evacuation system 1015 is shown leading out of the body cavity of the patient 1005.

The smoke evacuation system 1015 can be used in conjunction with the insufflation system 1001 described above or may be used with other suitable insufflation systems. The smoke evacuation system 1015 comprises a discharge or exhaust limb 1017, a discharge assembly 1019, and a filter 1021. The discharge limb 1017 connects between the filter 1021 and the discharge assembly 1019, which in use is located in or adjacent to the patient 1005 surgical site or peritoneal cavity. The discharge limb 1017 is a self-supporting tube (that is, the tube is capable of supporting its own weight without collapsing) with two open ends: an operative site end and an outlet end.

At least one embodiment includes the realization that the use of a variable-stiffness tube as the conduit 1013 can deliver humidified gases to the patient 1005 surgical site with minimized heat loss. This can advantageously reduce overall energy consumption in the insufflation system, because less heat input is needed to compensate for heat loss.

Methods of Manufacture

The conduit, sheath or both of the delivery tube may be manufactured according to a number of processes, adapted to provide for stiffness variation in the tube. The conduit and sheath may be formed by the same manufacturing method, or by different manufacturing methods. In some manufacturing methods, the tube and sheath may be integrated during the manufacturing method such that the sheath is connected to the conduit at numerous locations along the length of the tube or along one continuous spiral along the length of the tube. Alternatively, the sheath may freely surround the conduit and only connect with the conduit at or adjacent the end connectors.

Typically the conduit, the sheath, or both may be made from one or more extruded polymer components. The properties of the extrudate (including composition, surface-modifying agents, methods for increasing surface energy, and foaming agents) is described above.

A first manufacturing method is described with reference to FIG. 11. The method comprises extruding an elongate conduit having a longitudinal axis, a lumen extending along the longitudinal axis, and a wall surrounding the lumen, wherein the wall is stiffer in a first length of the conduit than in a second length of the conduit. The method can also involve corrugating the elongate conduit, such as with a corrugating die. More specifically, the process involves mixing or providing of a master batch of extrudate material (i.e. material for extrusion), feeding the master batch to an extrusion die head, extruding the extrudate as described above, and (optionally) feeding the elongate conduit into a corrugator using an endless chain of mold blocks to form a corrugated tube.

Figure 11:
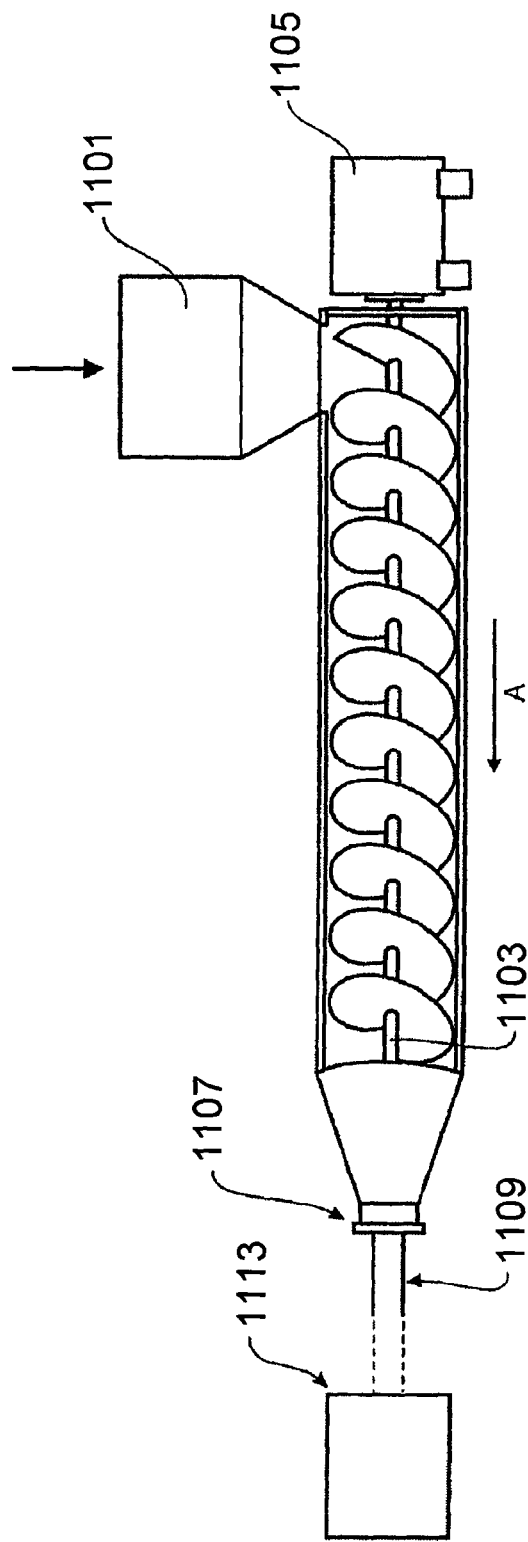
FIG. 11 is a schematic illustration of a manufacturing method for medical tubing, including hopper feed, screw feeder to a die head, and terminating with a corrugator.

FIG. 11 generally illustrates a setup where there is provided a feed hopper 1101 for receiving raw ingredients or material (e.g. master batch and other materials) to be passed through a screw feeder 1103 driven by a motor 1105 in direction A toward a die head 1107. The molten tube 1109 is extruded out of the die head 1111. Conductive filaments can optionally be co-extruded on or in the molten tube 1109. The method can further comprise one or more spiral-extrusion processes that progressively add layers of material in order to create portions of different stiffness along the tube. Such spiral-extrusion processes are described in greater detail below.

An extruder such as a Welex extruder equipped with a 30-40 mm diameter screw and, typically, a 12-16 mm annular die head with gap of 0.5-1.0 mm has been found to be suitable for producing low cost tubes quickly. Similar extrusion machines are provided by American Kuhne (Germany), AXON AB Plastics Machinery (Sweden), AMUT (Italy), and Battenfeld (Germany and China). A corrugator such as those manufactured and supplied by Unicor® (Hassfurt, Germany) has been found to be suitable for the corrugation step. Similar machines are provided by OLMAS (Carate Brianza, Italy), Qingdao HUASU Machinery Fabricate Co., Ltd (Qingdao Jiaozhou City, P.R. China), or Top Industry (Chengdu) Co., Ltd. (Chengdu, P.R. of China).

During manufacture, the molten tube 1109 is passed between a series of rotating molds/blocks on the corrugator after exiting the extruder die head 1111 and is formed into a corrugated tube. The molten tube is formed by vacuum applied to the outside of the tube via slots and channels through the blocks and/or pressure applied internally to the tube via an air channel through the center of the extruder die core pin. If internal pressure is applied, a specially shaped long internal rod extending from the die core pin and fitting closely with the inside of the corrugations may be required to prevent air pressure escaping endways along the tube. The corrugator speed can be varied to achieve different wall thickness. Slower corrugator speed gives a thicker wall, and faster speed gives a thinner wall.

The tube may also include a plain cuff region for connection to an end connector fitting. Thus, during manufacture, a molded-plastic end connector fitting can be permanently fixed and/or air tight by friction fit, adhesive bonding, over moulding, or by thermal or ultrasonic welding.

Figure 12:
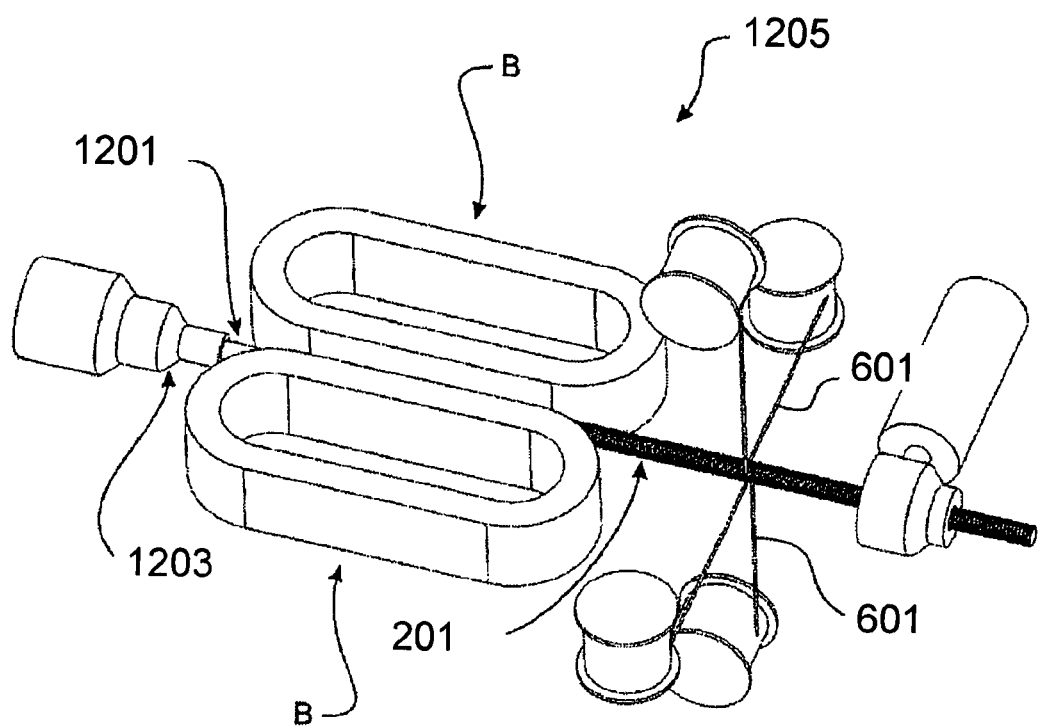
FIG. 12 is a schematic illustration of a spiral-forming manufacturing method for medical tubing.

Another suitable method for manufacturing a tube according to the embodiments described here involves spiral forming, as shown in FIG. 12. In general, the method comprises extruding a tape, wherein a first length of the tape is stiffer that a second length of the tape; spirally winding the extruded tape around a mandrel such that adjacent turns of the extruded tape touch or overlap, thereby forming an elongate conduit having a longitudinal axis, a lumen extending along the longitudinal axis, and a wall surrounding the lumen, wherein the wall is stiffer in a first length of the conduit than in a second length of the conduit. The method can also include optionally corrugating the elongate conduit.

The extrusion process involves mixing or providing of a master batch of extrudate material (i.e. material for extrusion), feeding the master batch to an extrusion die head, extruding the extrudate into a tape.

Then, the extruded or pre-formed tape is wound helically so that within each turn, one edge of the tape overlaps an edge of a preceding turn and underlaps an edge of a succeeding turn. Such spirally wound conduits can be made with a single helically disposed tape or multiple helically disposed tapes interleaved. In some embodiments, a reinforcing bead overlays the overlap between turns of tape. The bead may provide a helical reinforcement against crushing for the tube and may also provide a source of heat, chemical or mechanical adhesive for fusing or joining the lapped portions of tape. In some examples, a double wall conduit can be constructed by laying additional tape, or portions of the same tape, over the outside, supported on the helical ridge formed by the bead.

In this method, the stiffness of the tube depends upon the stiffness of the tape, and the stiffness of the tube can be adjusted by changing the thickness, mass, volume, flex modulus, etc. of the tape. A tube having variable wall thickness along its length may be constructed according to this process by varying the thickness of the tape so that, for example, in a first region, the tape may have a thickness that is greater than in another region, where the thickness may be slightly thinner, and the second region where the thickness may be thinner still.

Another suitable method for spiral forming comprises extruding a tape having a generally uniform stiffness; spirally winding the extruded tape around a mandrel such that adjacent turns of the extruded tape touch or overlap, thereby forming an elongate conduit having a longitudinal axis, a lumen extending along the longitudinal axis, and a wall surrounding the lumen, wherein the wall is stiffer in a first length of the conduit than in a second length of the conduit. The method can includes corrugating the elongate conduit, to provide a conduit having a variable-stiffness wall. For example, the corrugator speed can be varied to achieve different wall thickness. Slower corrugator speed gives a thicker wall, and faster speed gives a thinner wall.

Shown in FIG. 12 is a molten extruded tube 1201 exiting the die 1203 of an extruder before passing into a corrugator 1205. On exiting the corrugator 1205, a heater wire 601 is wound about the exterior of the formed tubular component 201.

One advantage of the preferred type of the tube manufacture described above with reference to FIG. 12 is that some of the mold blocks B can include end cuff features that are formed at the same time as the tubular component 201. Manufacture speeds can be significantly increased by the reduction in complexity and elimination of secondary manufacturing processes. While this method is an improvement over separate cuff forming processes, a disadvantage of the prior art plain cuff is that the corrugator must slow down to allow the wall thickness of the tube in this area to increase (the extruder continues at the same speed). The cuff thickness is increased to achieve added hoop strength and sealing properties with the cuff adaptor fitting. Further, the heat of the molten polymer in this thicker region is difficult to remove during the limited contact time with the corrugator blocks and this can become an important limiting factor on the maximum running speed of the tube production line.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention claimed is:

1. A medical tube for providing humidified gas to a patient, comprising:
a first connector;
a second connector;
an elongate conduit extending between the first connector and the second connector, the conduit having
a first end connected to the first connector,
a second end connected to the second connector,
a first opening at the first end, the first opening configured in size and shape to connect to a source of humidified gas such that the first opening receives humidified gases from the source of humidified gas,
a second opening at the second end, the second opening configured in size and shape to connect to a patient interface such that the second opening expels humidified gases to the patient through the patient interface,
a longitudinal axis,
a lumen extending between the first opening and the second opening along the longitudinal axis, and
an extruded wall extending between the first opening and the second opening and surrounding the lumen,
wherein a first portion of the extruded wall surrounding the first opening has a first stiffness and a second portion of the extruded wall surrounding the second opening has a second stiffness,
wherein the first stiffness is greater than the second stiffness, and wherein a third stiffness of a third portion of the extruded wall in a region of the conduit between the first portion and the second portion of the extruded wall is intermediate the first stiffness and the second stiffness.

2. The medical tube of claim 1, wherein the extruded wall comprises an extruded material which comprises one or more surface modification agents.

3. The medical tube of claim 1, wherein a thickness of the first portion of the extruded wall surrounding the first opening is between about 0.5 mm and about 2.0 mm, and a thickness of the second portion of the extruded wall surrounding the second opening is between about 0.1 mm and about 1.0 mm.

4. The medical tube of claim 1, wherein a mass of the first portion of the extruded wall surrounding the first opening is between about 50 g/m and about 110 g/m, and a mass of the second portion of the extruded wall surrounding the second opening is between about 20 g/m and about 50 g/m.

5. The medical tube of claim 1, wherein a volume of the first portion of the extruded wall surrounding the first opening is between about 1.0 cm$^3$/m and about 2.0 cm$^3$/m, and a volume of the second portion of the extruded wall surrounding the second opening is between about 0.2 cm$^3$/m and about 1.0 cm$^3$/m.

6. The medical tube of claim 1, wherein the ratio of flex modulus of the first portion of the extruded wall surrounding the first opening to flex modulus of the second portion of the extruded wall surrounding the second opening is between about 10:1 and about 250:1.

7. The medical tube of claim 1, wherein the extruded wall is a single piece of polymer foam formed by extrusion of a single extrudate.

8. The medical tube of claim 1, wherein the first portion of the extruded wall surrounding the first opening has a first thickness and the second portion of the extruded wall surrounding the second opening has a second thickness, wherein the first thickness is greater than the second thickness.

9. The medical tube of claim 1, wherein the first portion of the extruded wall surrounding the first opening is configured to extend vertically upward from the source of humidified gas without a support holding the first portion when the first opening is connected to the source of humidified gas, the first portion of the extruded wall defining a drain-back length.

10. The medical tube of claim 1, wherein the extruded wall is corrugated.

11. The medical tube of claim 1, wherein the first portion of the extruded wall surrounding the first opening is configured to extend vertically upward from the source of humidified gas, the first portion of the extruded wall defining a drain-back length.

12. The medical tube of claim 11, wherein the drain-back length is between about 350 mm and about 400 mm.

13. The medical tube of claim 1, further comprising one or more conductive filaments in or on the conduit.

14. The medical tube of claim 13, wherein at least one of the one or more conductive filaments is a heating wire.

15. The medical tube of claim 13, wherein at least one of the one or more conductive filaments is a sensing wire.

16. The medical tube of claim 1, wherein the extruded wall comprises an extruded material, wherein the extruded material is foam.

17. The medical tube of claim 16, wherein the foam is closed-cell foam.

18. The medical tube of claim 1, further comprising a sheath surrounding at least a portion of an outer surface of the elongate conduit.

19. The medical tube of claim 18, wherein the sheath comprises an extruded material extruded around at least a portion of the outer surface of the elongate conduit.

20. The medical tube of claim 18, wherein the sheath comprises a material generally spirally wrapped around at least a portion of the outer surface of the elongate conduit.

21. The medical tube of claim 18, wherein the sheath comprises a sleeve material sleeved around at least a portion of the outer surface of the elongate conduit.

22. The medical tube of claim 18, wherein the sheath comprises a sheath wall and the sheath wall is stiffer in a first region of the sheath than in a second region of the sheath.

23. The medical tube of claim 22, wherein the sheath wall is stiffer proximate the first opening of the conduit than the sheath wall proximate the second opening of the conduit.

24. The medical tube of claim 22, wherein the sheath wall is stiffer proximate the second opening of the conduit than the sheath wall proximate the first opening of the conduit.

\* \* \* \* \*